(12) United States Patent
Bourque

(10) Patent No.: US 10,471,223 B2
(45) Date of Patent: Nov. 12, 2019

(54) METHODS AND APPARATUS FOR PRODUCING HERBAL VAPOR

(71) Applicant: CannaKorp, Inc., Stoneham, MA (US)

(72) Inventor: Michael Patrick Bourque, Melrose, MA (US)

(73) Assignee: CannaKorp, Inc., Stoneham, MA (US)

(*) Notice: Subject to any disclaimer, the term of this patent is extended or adjusted under 35 U.S.C. 154(b) by 776 days.

(21) Appl. No.: 15/221,815

(22) Filed: Jul. 28, 2016

(65) Prior Publication Data
US 2016/0331913 A1 Nov. 17, 2016

Related U.S. Application Data

(63) Continuation of application No. PCT/US2015/013778, filed on Jan. 30, 2015.
(Continued)

(51) Int. Cl.
A61M 11/04 (2006.01)
A61M 15/00 (2006.01)
(Continued)

(52) U.S. Cl.
CPC ...... *A61M 15/0023* (2014.02); *A61M 11/003* (2014.02); *A61M 11/02* (2013.01);
(Continued)

(58) Field of Classification Search
CPC ............ A61M 15/0043; A61M 15/003; A61M 15/0063; A61M 15/06; A61M 15/0028;
(Continued)

(56) References Cited

U.S. PATENT DOCUMENTS 3,090,380 A 5/1963 Dold
6,158,428 A 12/2000 Mecikalski
(Continued)

FOREIGN PATENT DOCUMENTS

DE 43 28 243 C1 3/1995
EP 0 965 355 A2 12/1999
(Continued)

OTHER PUBLICATIONS

Extended European Search Report and Written Opinion for European Application No. 15742714.7, dated Feb. 26, 2018.
(Continued)

*Primary Examiner* — Tan-Uyen T Ho
*Assistant Examiner* — Margaret M Luarca
(74) *Attorney, Agent, or Firm* — Wolf, Greenfield & Sacks, P.C.

(57) ABSTRACT

The present disclosure relates to systems and methods for producing a consistent and effective herbal vapor. A sealed container pod may include a chamber wall defining an internal volume within which a pre-processed herbal composition (e.g., *cannabis*) is located. The container pod may include filters for the vapor produced from the herbal composition. The container pod may also include a support member for holding and evenly distributing the herbal composition within the internal volume during vaporization. A vaporizer may be configured to obtain information regarding the contents of the herbal composition. The vaporizer may expose the herbal composition to an automated series of timed temperature adjustments specifically tailored for producing a desirable herbal vapor. The herbal vapor may be collected into a bag and/or canister for subsequent consumption.

17 Claims, 28 Drawing Sheets

Related U.S. Application Data

(60) Provisional application No. 61/934,255, filed on Jan. 31, 2014.

(51) Int. Cl.
*A61M 11/02* (2006.01)
*A61M 11/00* (2006.01)

(52) U.S. Cl.
CPC ........ *A61M 11/042* (2014.02); *A61M 15/002* (2014.02); *A61M 15/0003* (2014.02); *A61M 15/0005* (2014.02); *A61M 15/0016* (2014.02); *A61M 15/0035* (2014.02); *A61M 15/0043* (2014.02); *A61M 15/0086* (2013.01); *A61M 15/0098* (2014.02); *A61M 2205/276* (2013.01); *A61M 2205/3334* (2013.01); *A61M 2205/3368* (2013.01); *A61M 2205/3553* (2013.01); *A61M 2205/3584* (2013.01); *A61M 2205/3653* (2013.01); *A61M 2205/505* (2013.01); *A61M 2205/6072* (2013.01); *A61M 2209/045* (2013.01)

(58) Field of Classification Search
CPC ... A61M 11/003; A24F 47/002; A24F 47/004; A24F 47/008; A24D 1/14
See application file for complete search history.

(56) References Cited

U.S. PATENT DOCUMENTS

| 9,433,241 | B2* | 9/2016 | Jalloul ............... A24D 1/14 |
| 2005/0172976 | A1 | 8/2005 | Newman et al. |
| 2007/0204512 | A1 | 9/2007 | Self et al. |
| 2009/0078253 | A1 | 3/2009 | Bao |
| 2010/0024834 | A1 | 2/2010 | Oglesby et al. |
| 2010/0322599 | A1 | 12/2010 | Landry |
| 2011/0308521 | A1 | 12/2011 | Kefford |
| 2012/0199572 | A1 | 8/2012 | Shen et al. |
| 2012/0255546 | A1 | 10/2012 | Goetz et al. |
| 2013/0087144 | A1* | 4/2013 | Todd ............... A61B 5/1171 128/203.14 |
| 2013/0276781 | A1 | 10/2013 | Steelman et al. |
| 2014/0053832 | A1* | 2/2014 | Postma ............... A24F 47/004 128/202.21 |

FOREIGN PATENT DOCUMENTS

| GB | 2 182 249 A | 5/1987 |
| WO | WO 95/27411 A1 | 10/1995 |
| WO | WO 2015/177263 A1 | 11/2015 |
| WO | WO 2015/198015 A1 | 12/2015 |

OTHER PUBLICATIONS

International Search Report and Written Opinion dated Jun. 26, 2015 from International Patent Application No. PCT/US2015/013778.
International Preliminary Report on Patentability dated Aug. 2, 2016 from International Patent Application No. PCT/US2015/013778.
Partial European Search Report for European Application No. 15742714.7, dated Oct. 11, 2017.

* cited by examiner

310

314

METHODS AND APPARATUS FOR PRODUCING HERBAL VAPOR

RELATED APPLICATIONS

This application is a continuation of International Application No. PCT/US2015/013778, filed Jan. 30, 2015, which claims the benefit of U.S. Provisional Application No. 61/934,255, filed Jan. 31, 2014, each of which is hereby incorporated by reference in its entirety.

BACKGROUND

1. Field

Aspects herein relate to methods and apparatuses for producing herbal vapor.

2. Discussion of Related Art

*Cannabis*, or herbal marijuana, and the vapor that is produced therefrom has long been found to provide medicinal benefits, such as in treating cancer, glaucoma, seizures, multiple sclerosis, epilepsy, cancer, HIV, amongst other ailments. A person receiving treatment from *cannabis* may experience a stimulation in appetite, pain relief, relaxation, reduced inflammation and/or other benefits. These effects are due, in large part, to cannabinoids, which are chemical compounds found in *cannabis*, that act on the cannabinoid receptor system of the brain. The cannabinoid receptor system is involved in a number of physiological processes including appetite, pain-sensation, mood and memory. Endocannabinoids are substances (e.g., neuromodulatory lipids) produced within the body that activate cannabinoid receptors. However, it may be desirable for the amount of endocannabinoids within the body to be increased. Hence, in some cases, the cannabinoids found in *cannabis* may serve to restore or reinforce the presence of endocannabinoids that may otherwise be lacking within the system.

In certain regions within the United States, physicians are able to prescribe the use of *cannabis* for patients. However, the ability for *cannabis* dispensaries to reliably distribute consistent amounts and types of *cannabis* having a particular level of therapeutic quality is limited. For instance, in consuming medical *cannabis*, patients are often left to acquire loose *cannabis* buds or leaves stored in an open bag, complete with sticks, seeds and other non-consumable debris. Safety concerns may arise when *cannabis* is obtained in this manner, due to risks of contamination, tampering, misrepresentation, etc. Such *cannabis* may also have a relatively short shelf-life and may be cumbersome to handle before use, for example, in having to separate sticks, seeds, debris, or in grinding and packing the *cannabis* into receptacles for subsequent consumption.

SUMMARY

The inventor has recognized that it would be advantageous to provide users (e.g., patients, consumers, recreational users) of herbal materials (e.g., vaporized, smoked, etc.) with a system that provides the ability to consume high-quality herbal vapor in a way that is safe, predictable and convenient. Accordingly, embodiments described herein relate to containers and vaporizers, and systems and methods for their use in producing herbal vapor that consistently and easily provides users with a substantially greater therapeutic/medicinal effect in comparison to existing methods.

In various embodiments, a sealed container pod may have a chamber wall defining an internal volume within which a pre-specified and processed amount and type of herbal composition (e.g., *cannabis*) is stored or otherwise located. The container may include one or more filters suitably positioned and constructed to filter vapor arising from the herbal composition. The container may further include a support member for holding the herbal composition during vaporization. The support member may be useful to keep the herbal composition evenly distributed within the container than would otherwise be the case without the support.

The container may be placed within the receptacle of a vaporizer configured to obtain information regarding the contents of the herbal composition (e.g., by reading markings on the surface of the container) and exposing the herbal composition to a recipe that may include a temperature profile specifically tailored for producing a desirable herbal vapor. Such a temperature profile may involve an automated series of timed temperature adjustments to which the herbal composition is subjected during a stage of herbal extraction. In some embodiments, the vaporizer may be programmed to flow air through the container and into a collection region, such as a bag or canister for containing the herbal vapor. In some embodiments, the canister holding the herbal vapor may be removed from the vaporizer, for portable consumption.

In an illustrative embodiment, a container for producing an herbal vapor is provided. The container may include a chamber having a wall defining an internal volume and a boundary that seals the internal volume from an external environment. The container may also include at least one filter located within the internal volume of the chamber constructed and arranged to filter vapor produced from the herbal composition. The container may further include a support member located within the internal volume of the chamber, for holding the herbal composition during vaporization.

In another illustrative embodiment, a vaporizer for producing an herbal vapor is provided. The vaporizer may include a receptacle for receiving a container including a chamber having a wall defining an internal volume. The vaporizer may also include an information reader configured to read information from a surface of the container regarding contents of an herbal composition located within the internal volume of the chamber. The vaporizer may include a heater for adjusting a temperature within the internal volume of the chamber based on the information read from the container, and a controller configured to control the heater to cause an automated series of timed temperature adjustments within the internal volume of the chamber for herbal extraction based on the information read from the container.

In yet another illustrative embodiment, a method for producing an herbal vapor from an herbal composition held within an internal volume of a chamber of a container is provided. The method may include providing information derived from a surface of the container regarding contents of the herbal composition held within the internal volume of the chamber to a controller. The method may also include flowing air through the internal volume of the chamber and into a collection region, and heating the internal volume of the chamber during air flow based on the information read from the container. The method may further include adjusting temperature within the internal volume of the chamber to exhibit an automated series of timed temperature adjustments within the internal volume of the chamber during herbal extraction based on the information read from the container.

Various embodiments of the present disclosure provide certain advantages. Not all embodiments of the present disclosure share the same advantages and those that do may not share them under all circumstances. Various embodiments described may be used in combination and may provide additive benefits.

Further features and advantages of the present invention, as well as the structure of various embodiments of the present disclosure are described in detail below with reference to the accompanying drawings.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. Various embodiments of the invention will now be described, by way of example, with reference to the accompanying drawings, in which.

DETAILED DESCRIPTION

Figure 1:
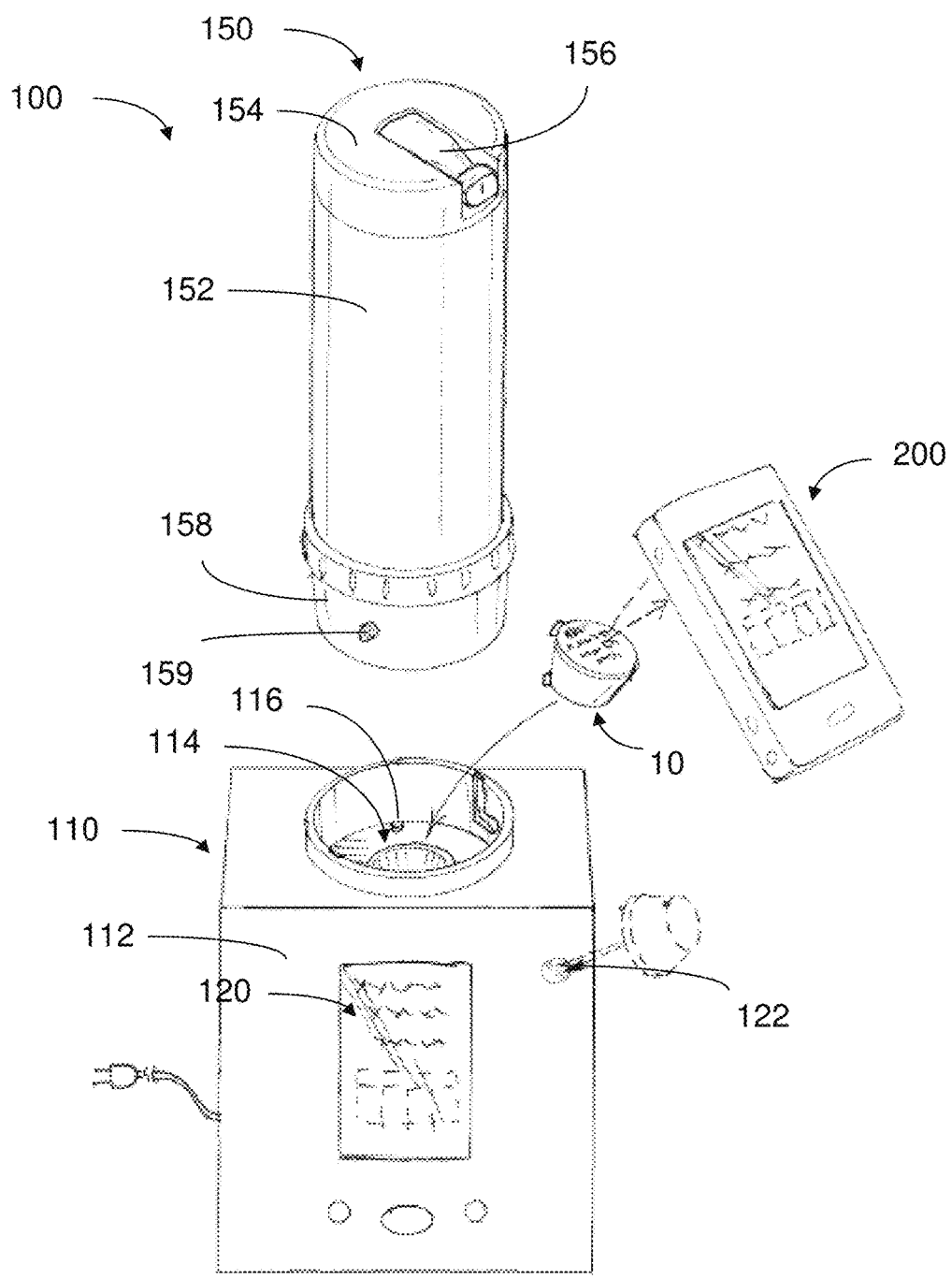
FIG. 1 depicts a perspective view of a vaporizer and a container system in accordance with an embodiment.

The present disclosure relates to a system that provides users with the ability to safely, reliably and conveniently obtain a high-quality, therapeutic herbal vapor, produced from an herbal composition, such as *cannabis*. In various embodiments, a sealed container pod, vaporizer and an overall system are provided for streamlining the consumption of herbal vapor in a consistently desirable and safe manner.

In some embodiments, a consumer may simply insert a container pod into a vaporizer receptacle (with the option for the vaporizer to remove the lid for the user), never having to measure, weigh, touch, grind, or risk spilling the herbal product to be vaporized and consumed. Similarly, aspects of the present disclosure may minimize or otherwise limit direct contact of the herbal product with packagers, retailers or other persons along the manufacturing and production chain, to reduce the potential for contamination thereof. The contents within the container pod may be subject to a recipe of conditions pre-specified for the contents of that particular container pod, in producing a suitable herbal vapor. Such an herbal vapor, when subject to the appropriate recipe, is produced with substantially the entirety of the active/therapeutic ingredients from the original herbal blend having been preserved and extracted.

As provided herein, an herbal composition may include matter derived from a plant, used for consumption, such as for medicinal, therapeutic, aromatic and/or culinary purposes. An example of an herbal composition that may be employed for medicinal and/or therapeutic purposes is *cannabis* or marijuana, which involves the use of various cannabinoid compounds, such as tetrahydrocannabinol (THC), cannabidiol (CBD), cannabinol (CBN), tetrahydrocannabivarin (THCV) and cannabigerol (CBG). Such compounds may be used for medical therapy in treatment of disease and/or to alleviate symptoms, for example, in reducing nausea/vomiting and treating pain and muscle tightness or stiffness. Other herbal compositions may also be possible. For example, the herbal composition may also include flavonoids, terpenoids, amino acids, proteins, sugars, enzymes, fatty acids, esters and/or other compounds. Or, the herbal composition may include any one or combination of tobacco, spice, tea, herbal extracts, leafy food products, etc. The resulting herbal composition, consumed as a whole, may synergistically provide a highly desirable medicinal and/or therapeutic effect for the consumer.

As also provided herein, a vapor may include a gaseous phase substance that has components which may also exist as a liquid and/or solid. The vapor may include a mist, aerosol and/or nebulized composition that includes fine solid and/or liquid particles suspended in a gas or, in some cases, the vapor may be substantially formed as a gas. Accordingly, an herbal vapor is a vapor extracted or otherwise derived from an herbal composition. For example, an herbal vapor may include a gaseous substance having small droplets of oil, water and/or other chemical compounds suspended therein. Vaporizers may be devices used to vaporize or nebulize the active ingredients of an herbal composition and/or other materials, for the purpose of inhalation. In some embodiments, the vaporizer is a nebulizer. In some cases, a vapor includes liquid (e.g., water, oil, etc.) particles mixed with hot ambient air, which is cooled down so as to condense into a fine cloud of visible airborne droplets. Accordingly, the active ingredients may be breathed or otherwise administered as medication and/or as therapy in a vaporized form.

In some embodiments, the container pod includes a chamber having a wall defining an internal volume for containing the herbal composition. A lid may provide a seal for the container so that the herbal composition located within the internal volume is isolated from the external environment and, for example, is kept from degrading. The sealed container may further provide quality control for the herbal composition, which may be pre-processed and packaged therein, providing consistency and reliability of its contents. The container pod may also provide an appropriate environment (e.g., dark, low in relative humidity, inert, etc.) to promote curing and/or decarboxylation of the herbal composition. Accordingly, the sealed container pod may provide the herbal composition with a relatively long shelf-life. Thus, container pods in accordance with the present disclosure may be kept for long periods of time without suffering degradation of the contents therein and, for example, may be easily transported, sold in stores, used in vending dispense machines, etc.

The container pod may further include readable information, for example, given by clear labelling (e.g., markings) on an exterior surface of the container, for providing to a user and/or system information regarding its contents. Such information may ultimately be relevant in subjecting the herbal composition to conditions that predictably result in a preferred herbal vapor, with consistency in effects/experience, quality, taste and/or smell.

The container may include a filtering mechanism, such as one or more filters located on either side of the herbal composition, for removing undesirable particulates and/or other contaminants from the herbal vapor as it travels away from the internal volume of the chamber and into a collection region.

The container may also include a support member to hold the herbal composition within the internal volume of the chamber during vaporization. The support member may suspend or otherwise distribute the herbal composition within the internal volume during exposure to vaporization heat.

In some embodiments, a vaporizer may be equipped with a controller that is configured to obtain information regarding the contents of the herbal composition based on the readable information. For instance, the vaporizer may have an information reader, such as a digital code reader (e.g., for bar codes, QR codes, etc.) for reading the readable information on the surface of the container and/or user interface, for providing input to the controller of the information about the herbal composition. Based on this input, the vaporizer may process the herbal composition within the chamber according to a specific vaporization recipe, to produce an herbal vapor having particularly desirable characteristics. For example, the vaporizer may flow air through the chamber as well as provide a temperature profile within the chamber for extracting a suitable combination of chemical compounds according to a specified protocol. In some embodiments, this temperature profile may include a number of timed temperature adjustments that occur during the period of vaporization when herbal extraction occurs. In some cases, the vaporizer may provide this temperature profile as part of an automated process of herbal vaporization and extraction, or a user may input such a profile into the vaporizer. Vapor generated from the herbal composition is then passed from the internal volume of the chamber to a bag, canister and/or other collection region, for consumption by a user.

FIG. 1 depicts an illustrative embodiment of a container 10 for holding an herbal composition and a vaporizer 100 having a base 110 including a housing 112 that further includes a receptacle 114, for receiving the container 10 and processing the herbal composition to produce a suitable herbal vapor. In this embodiment, the vaporizer 100 includes an interface 120 having display and control features for receiving input from a user to transmit commands to the system, as well as providing feedback or information to the user. For instance, such user input may provide signals to the controller, for adjusting one or more vaporization parameters, such as the rate of air flow, temperature, relative humidity and/or other characteristics of the internal volume of the chamber.

As discussed herein, the vaporizer 100, or another device 200 (e.g., portable/wireless device, phone, etc.), may be configured to obtain information regarding the contents of the herbal composition held within the container 10, for example, via labelling/markings located on an exterior surface of the container. Hence, the base 110 also includes a digital reader 122, which may be located on the exterior surface of the vaporizer (as shown). Alternatively, or in addition, a digital reader may be located at another region of the vaporizer, for example, at or near the receptacle 114 so that information regarding the container 10 may be obtained upon delivery. Based on this information, the vaporizer may then subject the herbal composition to a vaporization recipe which may include a temperature profile that is specially crafted for extracting a suitable combination of chemical compounds from the herbal composition, to achieve a balance that gives rise to a desired therapeutic result.

Any suitable information reader may be employed. As noted above, the digital reader may collect information from a surface of the container pod regarding the contents of the herbal composition and/or a preferred recipe for its vaporization. Based on markings on the surface of the container, the reader may provide a control unit of the vaporizer with any appropriate identification information (e.g., serial number, ingredients, herbal contents, strain information, chemical compound information, grower information, flavorings, weight, packing dates, use-by/expiration dates, patient/medical information, etc.) and/or vaporization information (e.g., cycle time, air velocity, air temperature, relative humidity, etc.) for the particular contents held within the container 10. The reader may also provide to the vaporizer identification information regarding the specific contents of the container pod. Accordingly, consumers are not left to guess the contents of the container pod, nor what vaporization recipe(s) apply.

As further shown, the vaporizer 100 may be equipped to receive a canister 150, or may have another type collection region, for collection and/or temporary storage of the herbal vapor produced from the container 10. In this embodiment, the canister 150 includes a housing 152, an upper cap 154 and a lower cap 158. The upper cap 154 includes a mouthpiece 156 through which a user may inhale vapor stored within an internal volume of the canister. The lower cap 158 may provide the canister with the ability to be suitably secured to the base 110. For example, the lower cap 158 may have a structure that complements the corresponding receiving area of the base 110.

In some embodiments, the lower cap 158 further includes a protrusion 159 that is biased outward so as to fit within a complementary insertion hole (not shown in the figures) within the receiving area of the base 110. Such a construction provides for the canister to be suitably held in place during operation of the vaporizer, while also allowing a user to easily remove the canister 150 from the base 110. It can be appreciated that any other suitable structure or feature may be used to hold or secure the canister or other collection member in place.

As further shown in FIG. 1, for some embodiments, the base includes a safety button 116 which may be used to prevent undesirable operation of the vaporizer 100. For example, when the safety button 116 is depressed, by appropriate placement of the canister, the vaporizer 100 (e.g., heater, pump, etc.) may be permitted to operate according to normal parameters. In contrast, when the safety button 116 is not depressed, various components of the vaporizer 100 may be effectively locked out.

Figure 2:
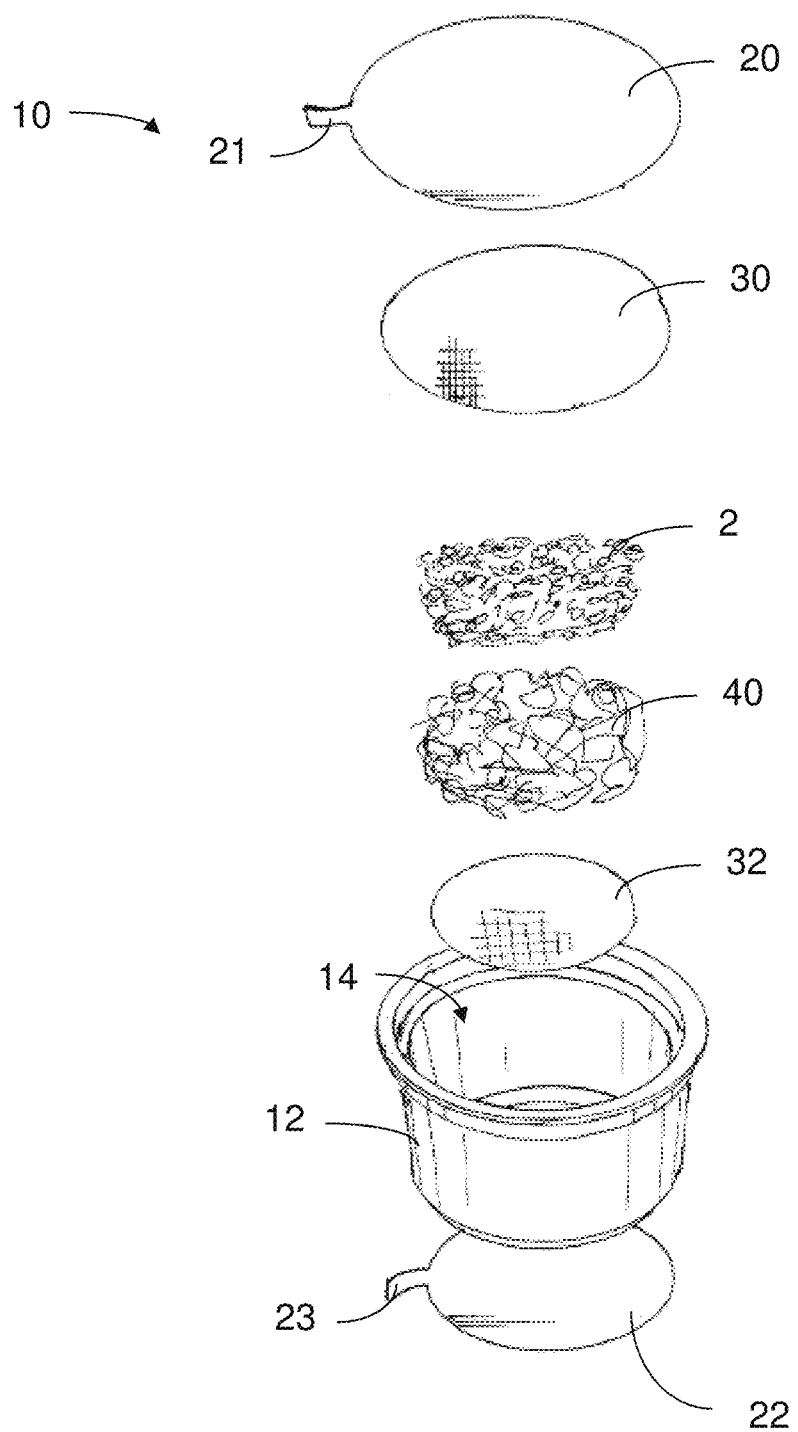
FIG. 2 shows an exploded perspective view of a container for holding an herbal composition in accordance with an embodiment.

FIG. 2 illustrates various components of an embodiment of the container 10, which includes a chamber having a wall 12 that defines an internal volume 14. The chamber of the container 10 may include any suitable material, such as for example, stainless steel, aluminium, silicone, glass, hemp, paper, plastic, polymer, other materials, or any appropriate combination thereof. For certain embodiments, the chamber may include a metallic material (e.g., steel, aluminium, etc.). Or, for some embodiments, the chamber may include a biodegradable and/or disposable material (e.g., hemp, paper, etc.). Other materials may be possible.

As shown, the container 10 includes an herbal composition 2 located within the internal volume 14. The herbal composition 2 may include *cannabis* having pre-specified amounts of cannabinoids, such as THC, CBN, CBD, amongst others. However, any appropriate blend of cannabinoids may be incorporated, according to any suitable combination, preferably to elicit a desired therapeutic response upon vaporization and consumption thereof.

The container 10 includes lids 20, 22 located on opposite ends of the chamber wall 12, forming a seal therewith, and enclosing the internal volume 14. As discussed herein, the sealed packaging of the herbal composition within the internal volume provides for easy storage and transport of the contents and predictability in their processing. The lids 20, 22 may include respective peel tabs 21, 23 for a user to easily remove the lids 20, 22 from the container, exposing the contents held therein. Though, it can be appreciated that for some embodiments, the lids 20, 22 may be automatically punctured and/or removed by the vaporizer, for example, via an appropriate piercing component provided in combination with the receptacle. Accordingly, for some embodiments, certain embodiments of containers may not require the use of peel tabs. Moreover, for certain embodiments, containers in accordance with the present disclosure do not require lids where the chamber wall may define an internal volume and a boundary that seals the internal volume from the external environment. For example, the chamber may be constructed as a ball or have another shape that does not have a lid, however, a portion of the chamber may be punctured and/or peeled to expose the contents of the container pod, for vaporization thereof.

The container pod may be sealed according to any suitable method. For example, the lid(s) may include foil, plastic or another appropriate material that is vacuum sealed on either end of the chamber wall 12. The lid(s) may be constructed for peeling away by a user prior to insertion into a vaporizer, or the lid(s) may be pierced by a component of the vaporizer itself. In some embodiments, the lid(s) may include further structure such as coupling features (e.g., threaded portions, elastomeric covers, etc.) for attaching to a complementary chamber wall. For example, when suitably coupled, the lid may form a seal with the chamber wall. Such a seal may be appropriate for locking in the overall aroma and freshness of the herbal composition, preserving the contents therein, as well as blocking external light and air, while sealed.

It can be appreciated that a number of different types, shapes, sizes of containers may be possible, for use in a variety of different vaporizing devices, as described further below. In various embodiments, the containers may include materials that exhibit high temperature tolerance, able to withstand relatively high heat temperatures.

To produce an herbal vapor with a desirable amount of potency and flavor, it may be preferable to cure the herbal composition (e.g., *cannabis*) before use. The container pod may provide the ability to pre-package the herbal composition in a manner that protects the herbal composition during storage and that promotes curing thereof. In some embodiments, the container may shield the herbal composition from certain conditions, while stored within the internal volume. For instance, exposure of the herbal composition to a particular degree of light, heat, humidity and/or oxygen may degrade the herb and ultimately reduce its overall potency when vaporized.

Conventionally, a user of *cannabis* would typically be required to obtain a particular strain of *cannabis* directly from a grower or distributer, store the *cannabis* in a relatively dry environment without contamination, process the *cannabis* by grinding and cleaning/removal of non-medicinal matter such as sticks and dirt, and then attempt to pack the *cannabis* into a vaporizer without significant loss. Such a process can be quite cumbersome, particularly for those that are unfamiliar with the wide variety of types of *cannabis* and/or how to effectively remove the non-medicinal materials from the raw *cannabis*. Otherwise, *cannabis* that is not processed and stored properly may degrade (e.g., dry out, grow mold, lose its medicinal qualities) and/or the full benefits of the *cannabis* may not be realized.

The ability to store, and seal within a controlled environment, a pre-processed *cannabis* composition within a labelled package provides a tremendous amount of benefit to users. For instance, such a container pod system provides the user with a level of convenience that had not previously been available, where the *cannabis* within the package comes pre-processed (e.g., ground, cleaned) and stored in a dry, secure, contamination-free environment. The seal may be tamper-resistant in revealing whether the container has been opened. This system also provides a greater degree of legitimacy where the user can be confident of the contents of the packaged product, as listed by the labelling.

In some embodiments, the container may include materials that are opaque, or non-light transmitting. For example, while closed (e.g., sealed), the container may prevent light from entering into the internal volume. As a result, while stored within the container, the herbal composition may be free from exposure to light, thus, reducing degradative effects that may arise due to the light.

In some embodiments, the internal volume within which the herbal composition is stored may be substantially removed of oxidizing or otherwise deleterious substances. For instance, prolonged exposure of the herbal composition to oxygen may have negative consequences and may reduce the overall quality of the herbal vapor produced therefrom. For example, exposure to oxygen may result in the occurrence of undesirable oxidation or other reaction(s), which may remove a number of desirable qualities from the herbal composition. To remove oxygen, an inert air (e.g., nitrogen gas, noble gas, etc.) may be flushed through the chamber. Accordingly, when suitably packaged, the herbal composition may be stored in a relatively inert environment substantially devoid of oxygen.

When appropriately packaged, the internal volume may also be maintained at a suitable level of relative humidity, as measured according to methods known in the art. It may be preferable for the herbal composition to be stored within a relatively dry environment, which may promote suitable curing and/or decarboxylation thereof, with little chance for degradation (e.g., mold growth, overdrying, spoilage, etc.). When the humidity level within the internal volume is relatively low, the herbal composition may be appropriately dried, allowing various oils/chemicals (e.g., provided from trichomes) of the herb to be exposed, for extraction thereof. In some embodiments, when sealed from the external environment, the relative humidity of the internal volume within which the herbal composition is stored may be maintained to be less than 80%, less than 70% (e.g., approximately 50-70%, approximately 60-70%, approximately 60-65%, approximately 62%), less than 60%, less than 50%, less than 40%, less than 30%, less than 20%, or less than 10%.

Similarly, when suitably packaged within the container pod, the moisture content of the herbal composition, as measured according to methods known in the art, within the internal volume may be maintained within a desired range. In some cases, it may be preferable for the moisture levels of the herbal composition to be low enough so as not to promote the growth of mold, or encourage the collection of harmful toxins. It may also be preferable for the moisture levels of the herbal composition to be high enough such that the buds do not become detrimentally dry and lose their medicinal qualities. In some embodiments, the moisture content of the herbal composition stored within the container pod is greater than 5%, greater than 8% (e.g., approximately 8-12%, approximately 8-10%), greater than 10%, greater than 12%, greater than 15%, or greater than 20%; or less than 20%, less than 15%, less than 10%, less than 8%, or less than 5%.

Providing the *cannabis* within a contained environment also alleviates the user of the need or desire to clean the vaporizer before or after usage. When *cannabis* is loosely loaded into the receptacle of a vaporizer, a substantial amount of unusable debris is typically left behind. Moreover, exposing the *cannabis* to excessive amounts of heat, which is often the case in conventional methods of vaporization, leads to the accumulation of a sticky tar-like residue within the vaporizer, which is difficult to remove from various components of the machine.

As further shown, the container 10 further includes filters 30, 32 located adjacent the lids 20, 22, within the internal volume 14, for filtering vapor that arises from the herbal composition upon heating thereof. For instance, the filter(s) may be constructed to trap unwanted particles that may arise during vaporization of the herbal composition. However, in some instances, it may be preferable for the filter(s) to be constructed such that the herbal composition, or derivatives therefrom (e.g., oils, residue, vapor, etc.), does not clog the filter(s). In some embodiments, the filter(s) may include a fine mesh that allows vapor produced from the herbal composition to pass freely therethrough, for example, without an undesirable amount of condensation or accumulation of debris. As shown, the outer mesh filter(s) may be removable as needed, optionally providing user access to the herbal composition.

It can be appreciated that other filter arrangements may be used. In some embodiments, one or more of the filters may be part of the chamber. For example, the filter(s) may be attached or integrally built in with the chamber wall such that the chamber itself has a base adjacent the lower lid 22 and/or adjacent the upper lid 20 which serves to filter air and/or vapor as it passes through the internal volume. In some cases, the chamber wall itself is provided as a filtration material that fully encloses the internal volume.

The filter(s) of the container may be constructed in any suitable manner. In some embodiments, the filter(s) may include a woven stainless steel wire screen mesh filter (e.g., woven stainless steel wire mesh filter having the following specifications, as understood by those skilled in the art, 100 Mesh, 0.0045" Wire, 0.0055" Opening, 36.0000" Width× 1200.0000" Length Coil), though, any suitable filter may be employed. For instance, the filter may include a fibrous cloth (e.g., hemp cloth) or other fabric.

The filter may have a suitable average pore size. In some embodiments, the average pore size of the filter is greater than 1 mil, greater than 5 mil, greater than 10 mil, greater than 20 mil, greater than 30 mil, greater than 40 mil, greater than 50 mil, or less than 50 mil, less than 40 mil, less than 30 mil, less than 20 mil, less than 10 mil, less than 5 mil, or less than 1 mil. Any suitable combination of the above-noted ranges, or values outside of these ranges, for the average pore size of the filter may be possible.

The filter(s) of the container may include an appropriate combination of characteristics that allow for vapor to pass freely through the filter while filtering out larger particles. In some embodiments, the filter has an average pore size of at least 10% smaller, at least 20% smaller, or at least 30% smaller than the average particle size of the herbal composition.

The container 10 may further include a support member 40 located within the internal volume 14 of the chamber. In some embodiments, the support member 40 may suitably hold or suspend the herbal composition 2 within the internal volume of the chamber during vaporization. That is, rather than allowing the herbal composition to collect or accumulate at the bottom of the container, the support member 40 may provide a scaffolding or other framework upon which the herbal composition may be supported, suspended or otherwise distributed within the internal volume 14. Such distribution allows the herbal composition to be heated in a relatively even manner during vaporization, resulting in a greater degree of herbal extraction than would otherwise be the case.

The container 10 may include any suitable support member 40 located within the internal volume 14 of the chamber. In some embodiments, the support member includes stainless steel wool, a coiled structure, a biasing or spring-like element, a metallic ribbon, a plurality of mesh screens, built-in shelving, a mesh bag, silicon, a hemp divider, ceramic, ball bearings (e.g., for agitation and grinding), a paper filter and/or any other appropriate support structure. The support member may include any appropriate material, such as metal, steel, carbon fiber, elastic material, polymeric material, plastic and/or any other suitable material.

As discussed above, the support member 40 may provide the ability to agitate and/or grind the herbal composition within the container. In some embodiments, the support member includes a number of ball bearings that can themselves be agitated such that contact of the herbal composition therewith may result in grinding of the herbal composition into smaller particles. Such grinding may allow for the contents of the herbal composition to be more exposed and/or better extracted than would otherwise be the case.

In some embodiments, the support member may be able to produce heat, via electromagnetic induction. That is, the vaporizer may include electromagnetic coils or other material(s)/structure(s) that are capable of creating a variable magnetic field that causes the support member to generate thermal energy. For example, a support member including a stainless steel wool/ribbon located within a sealed container pod may be susceptible to heating via induction from an electromagnetic field generated by coils located outside of the container pod. Accordingly, the support member itself may be used to heat the herbal composition located within the internal volume of the chamber, for example, according to a desired temperature profile.

In some embodiments, to ensure that the contents held within the container pod are well distributed throughout the internal volume of the chamber, the container pod may be suitably agitated. In some cases, an herbal composition may have a tendency to cake or clump together in a way that makes it more difficult to vaporize and ultimately extract therapeutic ingredients therefrom. Accordingly, the container pod may be shaken, compressed, squeezed, pinched and/or agitated in any suitable way to distribute the contents therein. In some cases, an herbal composition may have a tendency to clump or collect in a way that limits the potential of herbal extraction that is otherwise able to occur.

Figure 3A:
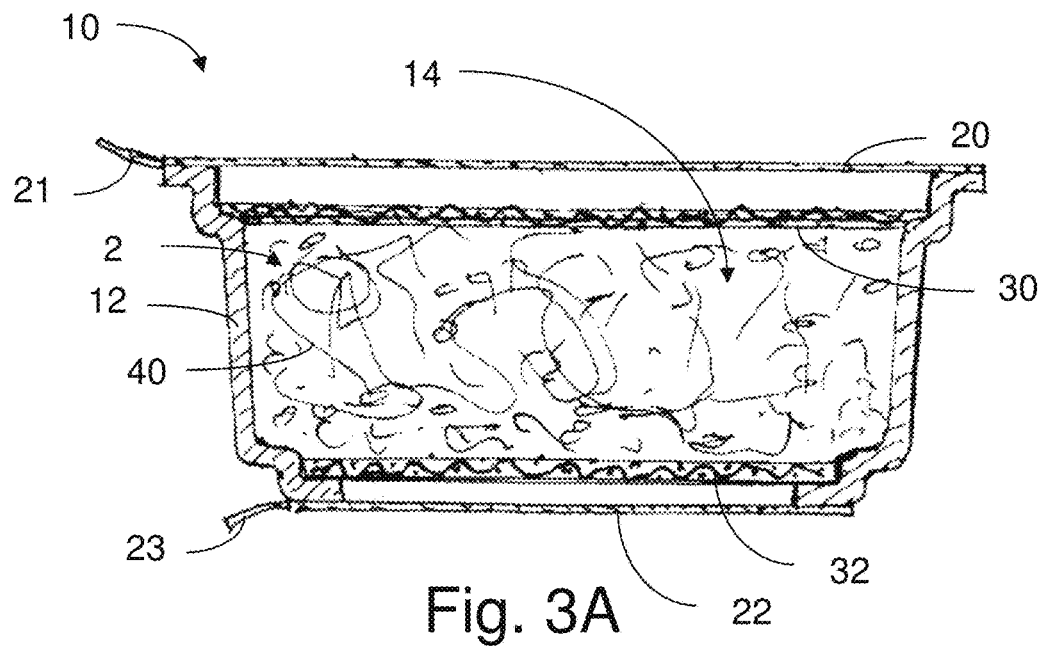
FIGS. 3A-3B illustrate various cross-sectional views showing agitation of a container for holding an herbal composition in accordance with an embodiment.
Figure 3B:
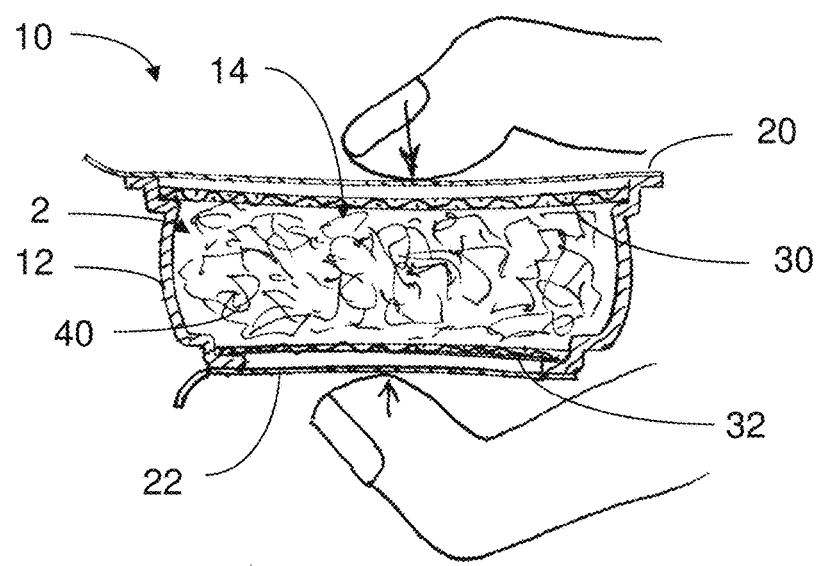

As shown in FIGS. 3A-3B, the container may have relatively flexible walls that allow the container to be pinched or agitated in an appropriate manner, which allows the ingredients therein to be freshened, re-distributed and/or broken down into comparatively finer and/or well-distributed particles, resulting in the potential for a greater amount of flavor(s) and chemical compounds available for extraction than would otherwise occur. As provided below, the support member may have the ability to recoil, so as to preserve the overall shape of the container upon loading.

Figure 4:
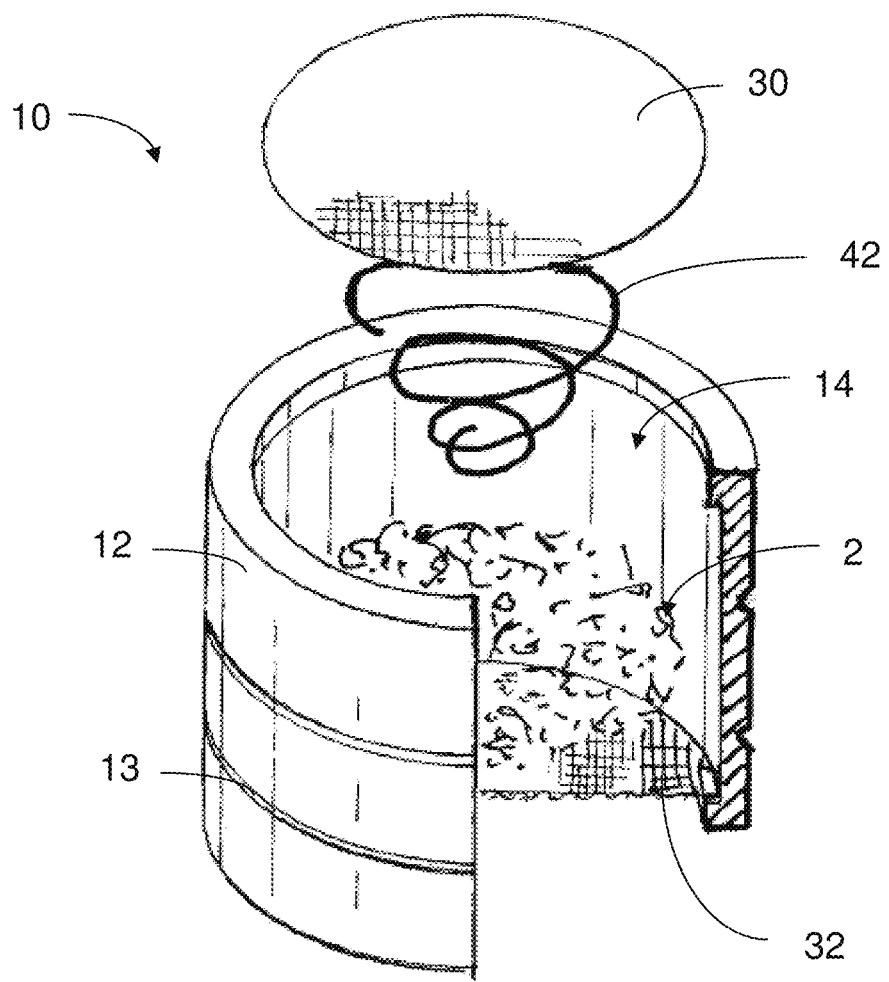
FIG. 4 shows a perspective cut-away view of another container for holding an herbal composition in accordance with an embodiment.

FIG. 4 depicts another illustrative embodiment of a container 10 having a spring-like support member 42. As shown, this support member 42 includes a thinly-wound metal coil that is able to hold the herbal composition 2 as it collects thereon, and may further allow the herbal composition to be broken down further when the container is pinched and/or squeezed. The spring-like nature of the coil also provides the container with structural stability when it is compressed or otherwise deformed, maintaining the overall shape of the container.

In the embodiment of FIG. 4, the outer surface of the chamber wall 12 includes grooves 13 that may serve as connection features for a receptacle of a vaporizer. For instance, the receptacle of the vaporizer may include protrusions that are complementary with the grooves, which allow for the container to be positioned securely therein, for herbal vaporization/extraction. It can be appreciated that any suitable connection features may be used between the container 10 and an appropriate receptacle of a vaporizer.

Figure 5:
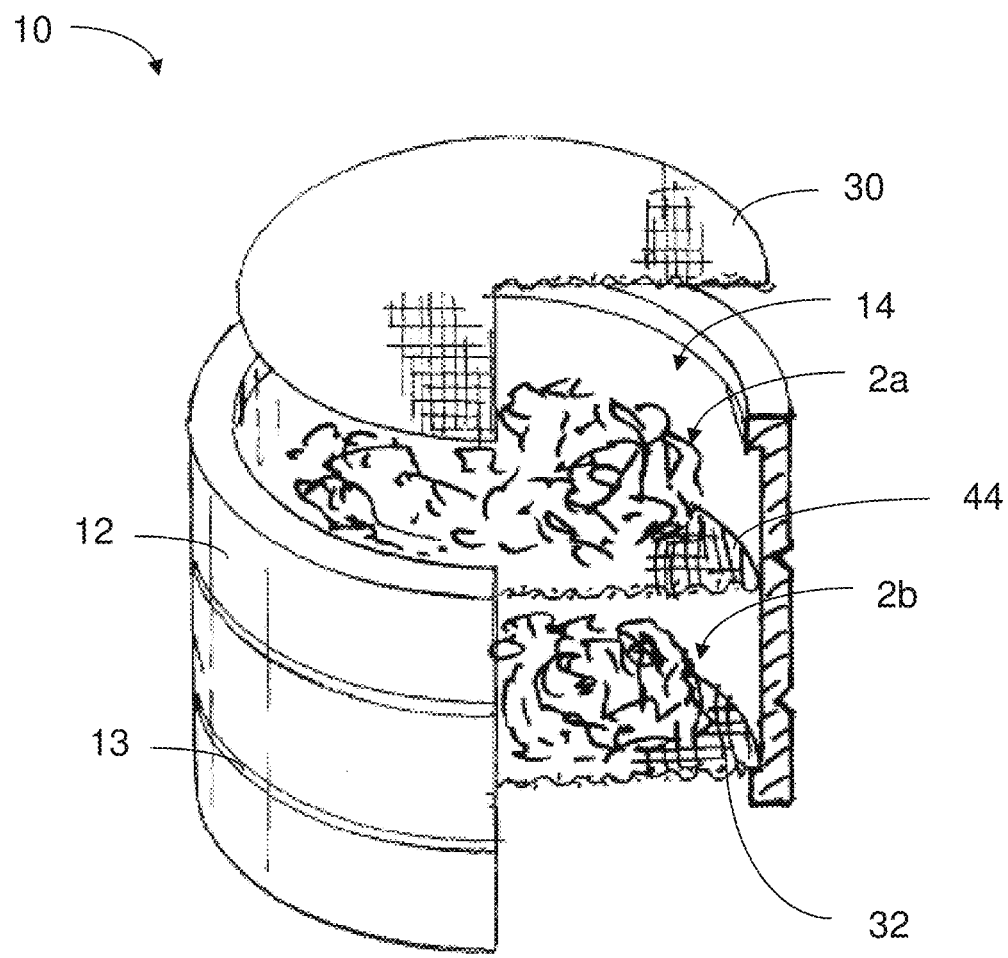
FIG. 5 depicts a perspective cut-away view of yet another container for holding an herbal composition in accordance with an embodiment.

FIG. 5 shows an illustrative embodiment of a container 10 having a support member 44 that includes a stacked mesh filter arrangement. For some embodiments, such a stacked mesh filter arrangement may also serve to hold and distribute the herbal composition within the internal volume. Such a stacked mesh filter arrangement may incorporate any appropriate number and type of filter. The mesh filter support member 44 may be similar or different from the filters 30, 32 on either side of the chamber.

In some cases, the additional mesh filter(s) may form compartments within the internal volume, dividing the herbal composition therein. Such a stacked filter mesh arrangement furthers allows for multiple ingredients to be stored within the internal volume, between filter meshes, for example, different types of medicinal strains and/or flavor enhancers, providing for novel and/or custom recipes for the consumer. Although, it may be possible for portions of the herbal composition to migrate from one compartment to another, particularly as the container is agitated. By holding and distributing the herbal composition within the internal volume, the support member 44 may also facilitate the temperature distribution of the herbal composition to be relatively evenly distributed throughout during vaporization.

Figure 6:
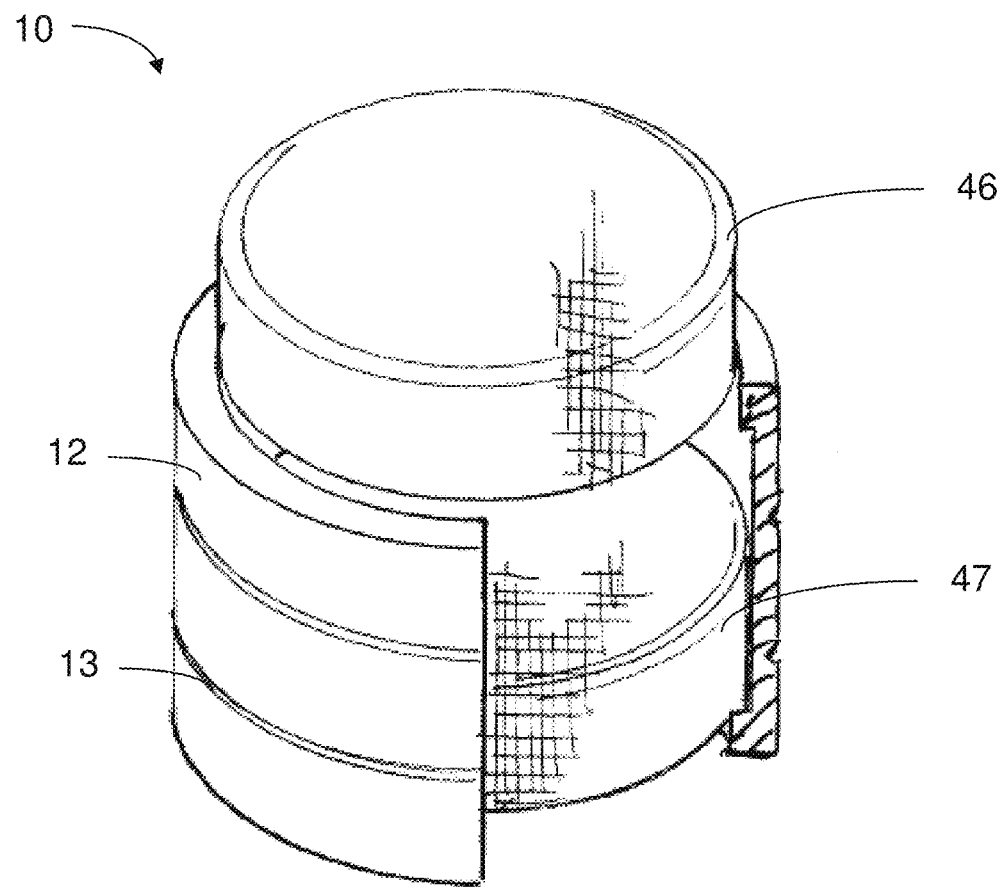
FIG. 6 shows a perspective cut-away view of another container for holding an herbal composition in accordance with an embodiment.

In another embodiment, shown in FIG. 6, the herbal composition is held within one or more flexible mesh bags 46, 47, which may provide a similar function to that of the stacked mesh filter arrangement(s) discussed above. Though, in this embodiment, the mesh bags allow for different herbal compositions to be pre-packaged or pre-loaded prior to incorporation within the container/pod system, allowing for relatively straightforward manufacturing thereof. That is, the pre-loaded bags may be prepared or otherwise provided from a separate manufacturing process, and then during manufacture of the container/pod, the bags each containing an appropriate herbal blend may be inserted into the space defined by the chamber. In accordance with various features described herein, the bag(s) may also be structured such that the herbal composition is held or otherwise evenly distributed throughout the internal volume, as well as allow for suitable agitation.

The container may have any appropriate shape or structure. For example, the chamber wall may have a cylindrical shape, a conical shape, a domed shape and/or a tapered construction. In some cases, the particular shape or structure of the container may allow it to be suitably placed within a complementary receptacle of a vaporizer. The shape/structure of the container may also provide for a suitable funneling or Venturi effect of the vapor. For instance, an upper end of the container may be tapered or dome-shaped such that vapor arising from the chamber is funneled upward toward an opening and into a collection area (e.g., bag, canister, mouthpiece, flow tube, etc.) where the vapor may be stored or otherwise contained for subsequent consumption.

Figure 7:
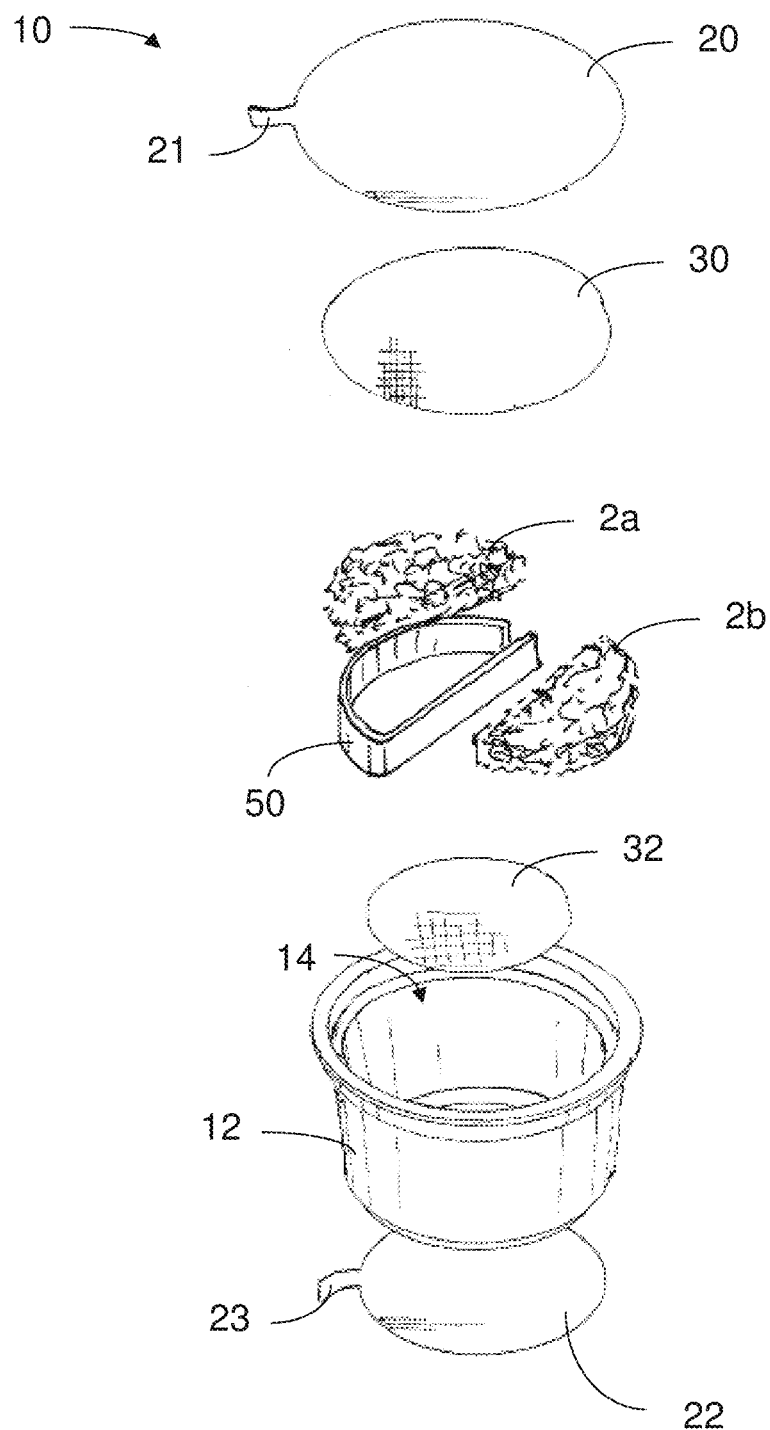
FIG. 7 shows an exploded view of a container for holding an herbal composition in accordance with an embodiment.

As discussed above, the internal volume of the chamber may be divided into separate compartments. FIG. 7 depicts an illustrative embodiment of a container 10 which includes a divider 50 that keeps different herbal compositions 2a, 2b physically separate from one another within the internal volume. In some cases, the divider 50 seals the separate compartments and, hence, herbal compositions 2a, 2b, from one another. Though, in other instances, a small amount of mixing between the herbal compositions 2a, 2b may occur, for example, during agitation of the container.

In some cases, it may be preferable to provide a container pod that holds a number of different herbal compositions (e.g., having varying types/blends) inside. And it may be further preferable for these different herbal compositions to be kept separate during storage. In some embodiments, the container pod includes a dividing wall that partitions the internal volume of the chamber into multiple sub-chambers or compartments. For example, the container and the vaporizer may be arranged such that only one of the different types/blends of herbal compositions is vaporized at a time. Or, vaporization may occur in succession, where the process of vaporization/extraction occurs for each of the herbal compositions during offset time periods. In some cases, it may be preferable for the vaporizer to have multiple lines through which separate parts of the chamber may be subject to herbal vaporization and extraction. That is, different compartments of the container may be individually heated and subject to separate air flows, allowing for more customized vapors to be produced, with blending of the ingredients at different times during the vaporization process.

Figure 8:
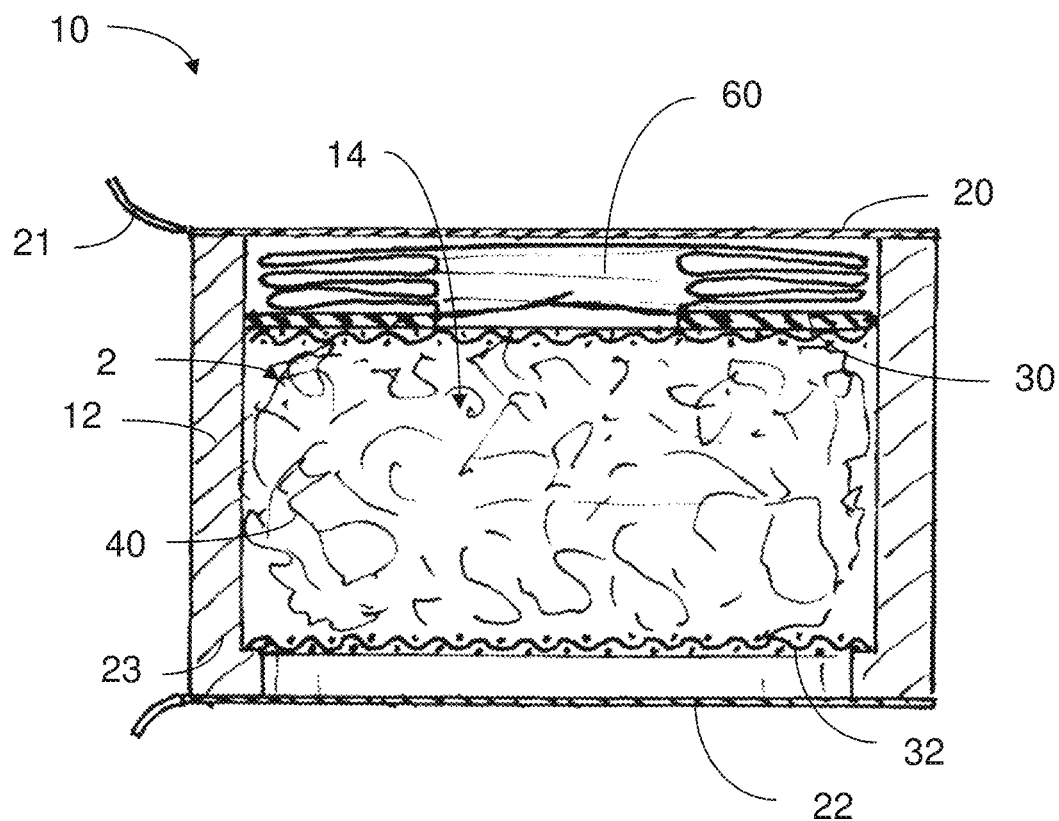
FIG. 8 depicts a cross-sectional view of a container for holding an herbal composition in accordance with an embodiment.

In another embodiment, a pod can have a balloon/bag built-in and/or snapped on for use in such vaporizers. This could be used instead of a bag that comes with or is otherwise supplied along with the vaporizer, and would add to the simplicity of using the pods. FIG. 8 depicts a container 10 having a bag 60 that is built in to the overall construction of the container. As shown, the bag 60 may enclosed within the internal volume 14 of the chamber, adjacent the sealed lid 20. Accordingly, during use, air flows through the bottom of the container and upward through the internal volume 14. The vapor produced therefrom is then collected into the bag 60, which expands out from the container and into an optional canister or other collection region of the vaporizer.

As discussed herein, the herbal composition may be prepared for storage and/or curing within the container in any suitable manner. In some embodiments, the herbal composition may be agitated, ground, fragmented, sliced and/or otherwise processed into fine particles which, in some cases, may allow for the medicinal and therapeutic qualities of the composition to be more easily extracted therefrom. The herbal composition may be fragmented or processed by any suitable method to achieve a desired size distribution, for example, via agitation of ball bearings, mortar and pestle, application of sonic energy, blender, slicing tool, processor, etc.

As discussed herein, as part of the packaging process, it may be preferable for the herbal composition (e.g., *cannabis*) to be cured and/or pre-processed to promote curing within the container. For certain embodiments, curing of the herbal composition may improve the overall quality of the vapor produced therefrom. For example, curing of *cannabis* may ultimately make available various flavors, aromas and potency of the *cannabis* during vaporization that would otherwise be unavailable without the curing process. That is, *cannabis* that is improperly cured can lose a significant amount of its desirable qualities when vaporized. Curing of *cannabis* may involve a drying process of the plant to remove or break down sugar and/or chlorophyll which may otherwise interfere with the overall quality of the herbal vapor. Appropriate curing may also be effective to expose trichomes of the *cannabis*, from which a substantial amount of cannabinoids and terpenoids may be extracted.

In some embodiments, curing of *cannabis* involves a slow, deep drying process (e.g., over the course of several days, approximately a week, or as long as a month) that allows the buds to dry while limiting the potential for mold to grow thereon. In some cases, when drying occurs too quickly (e.g., overheating, microwave, dehydrator, etc.), the buds may become relatively brittle, having a tendency to crumble, resulting in the suppression of trichome presentation from the plant, losing much of the flavor, aroma and potency that would otherwise be available. In a typical curing process, the branches and leaves are cut down and hung or laid out to dry on a mesh or rack. For high humidity environments, it may be preferable to cut down individual buds and lay them out to dry, at least in part, so as not to promote the growth of mold. However, separating out individual buds in a significantly low humidity environment may result in drying of the buds too quickly. In some embodiments, the buds are left to dry in an environment having a relative humidity of between 50-70% (e.g., approximately 60-62%).

In some cases, buds may be considered to be sufficiently cured when the buds achieve a sticky or tacky feel to the user, yet still able to move independently without substantial clumping in large bunches, for example, upon shaking. Further, the *cannabis* buds may be sufficiently removed of water so as to minimize the risk of mold growth. Once the buds are suitably cured, the buds are placed within the internal volume of container along with the appropriate support member. In some embodiments, the herbal composition is distributed throughout the internal volume, for example, by agitation/shaking in the presence of the support member. The container is subsequently removed of oxygen (e.g., air evacuation, flushing with a suitable inert gas) and then sealed.

The container pod may include any suitable herbal composition, pre-processed and packaging according to desired specifications. Accordingly, as discussed herein, consumers are able to know the exact contents within the container pod and, hence, can subject the pod to conditions that yield a desirable herbal vapor, having suitably extracted the active ingredients intact. By contrast, consumers employing conventional methods of herbal consumption often are unaware of the exact contents of the herbal composition that is being consumed. Such methods also typically require the consumer to process the herbal composition, leading to alterations and often denaturation of the herbal content, which may detrimentally affect the active ingredients.

In various embodiments, the herbal composition includes *cannabis*, which is often consumed for its psychoactive and physiological effects, such as heightened mood, euphoria, relaxation and increased appetite. In particular, *cannabis* has cannabinoids which provide a variety of medicinal qualities beneficial to the user, for example, antiemetics, antispasmodics, analgesics, amongst others. There are a number of different types of *cannabis* strains that produce therapeutic amounts of psychoactive cannabinoids, in particular, *Cannabis indica*, *Cannabis sativa* and *Cannabis ruderalis*. *Cannabis* has a multitude of active chemical compounds, including THC, which is the primary psychoactive constituent, and CBD, which is non-psychotropic yet has a number of medicinal qualities. For example, CBD has been prescribed to relieve convulsions, inflammation, cough, congestion, nausea, amongst others.

As discussed herein, container pods in accordance with the present disclosure may include an herbal composition having any suitable combination of ingredients/compounds. For instance, the herbal composition may include a particular combination of cannabinoids (e.g., THC, CBD, CBN, etc.), though, other ingredients and compounds (e.g., terpenes, flavonoids, etc.) may also be possible.

In some embodiments, the container pod includes a THC content of greater than 0.1 wt %, greater than 1.0 wt %, greater than 2.0 wt %, greater than 3.0 wt %, greater than 4.0 wt %, greater than 5.0 wt %, greater than 7.0 wt %, greater than 10.0 wt %, greater than 13.0 wt %, greater than 15.0 wt %, greater than 20.0 wt %, greater than 25.0 wt %, greater than 30.0 wt %, greater than 35.0 wt %, greater than 40.0 wt %; or less than 50.0 wt %, less than 40.0 wt %, less than 35.0 wt %, less than 30.0 wt %, less than 25.0 wt % (e.g., between approximately 15-25 wt %), less than 20.0 wt % (e.g., between approximately 10-20 wt %), less than 15.0 wt %, less than 13.0 wt %, less than 10.0 wt % (e.g., between approximately 1-10 wt %), less than 7.0 wt % (e.g., between approximately 2-7 wt %), less than 5.0 wt %, less than 4.0 wt %, less than 3.0 wt %, less than 2.0 wt %, or less than 1.0 wt %. Combinations of the above-noted ranges, or values outside of the these ranges, may be possible for the THC content of the container pod.

In some embodiments, the container pod includes a CBD content, a CBN content, or a combined CBD and CBN content of greater than 0.1 wt %, greater than 1.0 wt %, greater than 2.0 wt %, greater than 3.0 wt %, greater than 4.0 wt %, greater than 5.0 wt %, greater than 7.0 wt %, greater than 10.0 wt %, greater than 13.0 wt %, greater than 15.0 wt %, greater than 20.0 wt %, greater than 25.0 wt %, greater than 30.0 wt %, greater than 35.0 wt %, greater than 40.0 wt %; or less than 50.0 wt %, less than 40.0 wt %, less than 35.0 wt %, less than 30.0 wt %, less than 25.0 wt % (e.g., between approximately 15-25 wt %), less than 20.0 wt % (e.g., between approximately 10-20 wt %), less than 15.0 wt %, less than 13.0 wt %, less than 10.0 wt % (e.g., between approximately 1-10 wt %), less than 7.0 wt % (e.g., between approximately 2-7 wt %), less than 5.0 wt %, less than 4.0 wt %, less than 3.0 wt %, less than 2.0 wt %, or less than 1.0 wt %. Combinations of the above-noted ranges, or values outside of the these ranges, may be possible for the CBD content, CBN content or combined CBD/CBN content of the container pod.

Container pods in accordance with the present disclosure may include any suitable combination of chemical compounds, for example, THC, CBD, CBN and/or other ingredients. For example, container pods may include a THC content of less than 25.0 wt %, and a combined CBD and CBN content of less than 25.0 wt %. In some cases, the content of the container pods may be tailored according to the desired therapeutic/medicinal effect.

For instance, container pods that are intended to produce an herbal vapor that elicits a more psychoactive feeling of euphoria may have a relatively high THC content. As an example, such a container pod may include a THC content of between approximately 15-25 wt % (e.g., approximately 18-22 wt %) and a combined CBD and CBN content of less than approximately 2.0 wt % (e.g., less than 1 wt %).

Or, container pods that are customized to produce an herbal vapor that has a more medicinal effect, more often prescribed by physicians, may have a relatively high CBD or CBN content. In an example, such a container pod may include a THC content of between approximately 1-10 wt % (e.g., approximately 1-7 wt %, 2-7 wt %, approximately 5 wt %) and a combined CBD and CBN content of between approximately 10-20 wt % (e.g., approximately 13-20 wt %, approximately 15-18 wt %, approximately 17 wt %). Or, the container pod may include a THC content of between approximately 0.1-5.0 wt % (e.g., approximately 0.5 wt %) and a combined CBD and CBN content of between approximately 10-20 wt % (e.g., approximately 13-20 wt %, approximately 17 wt %).

In some cases, container pods may be intended to result in an herbal vapor having a hybrid of psychoactive and medicinal effects. For example, a container pod may include a THC content of approximately 10-20 wt % (e.g., approximately 14-17 wt %) and a combined CBD and CBN content of approximately 10-20 wt %, or less than approximately 10 wt % (e.g., less than approximately 1-2 wt %).

It can be appreciated that container pods may include any other suitable combination of ingredients, as the present disclosure is not limited to THC, CBD, CBN, or other compounds/ingredients. Further, the container pod may include herbal compositions having any appropriate form or make up, such as particulate (e.g., ground, sliced particular/leaves, pulp), viscous (e.g., oils, wax, liquid), or any other substance. For example, the herbal composition may include ice hash, water hash, resin, hemp, etc.

While some embodiments of the container pod may contain *cannabis* in a suitable amount, it can be appreciated that pods and various components described herein may be used for substances other than *cannabis*, such as other leafy products, medicines, therapeutic compositions, herbal products (e.g., tobacco), food (e.g., tea), etc. The herbal composition may further include flavorings (e.g., terpenes, flavonoids, mint, chamomile, ginko, mango, etc.), and other additives/ingredients, as suitably desired.

The herbal composition within the container pod may have a suitable average particle size. In some embodiments, the average particle size of the herbal composition within the internal volume of the container may be greater than 1.0 micron, greater than 10 microns, greater than 50 microns, greater than 100 microns, greater than 200 microns, greater than 300 microns, greater than 400 microns, greater than 500 microns, greater than 600 microns, greater than 700 microns, greater than 800 microns, greater than 900 microns, greater than 1.0 mm, greater than 2.0 mm, greater than 3.0 mm, greater than 4.0 mm, greater than 5.0 mm, or greater than 10.0 mm; or less than 20.0 mm, less than 10.0 mm, less than 5.0 mm, less than 4.0 mm, less than 3.0 mm, less than 2.0 mm, less than 1.0 mm, less than 900 microns, less than 800 microns, less than 700 microns, less than 600 microns, less than 500 microns, less than 400 microns, less than 300 microns, less than 200 microns, less than 100 microns, less than 50 microns, less than 10 microns, or less than 1.0 micron. Any suitable combination of the above-noted ranges, or values outside of these ranges may be possible for the average particle size of the herbal composition.

It can be appreciated that container pods in accordance with the present disclosure may be constructed in any suitable configuration. In some embodiments, the container pods may be stackable and/or may couple with one another, for storage or manufacturing. Or, in some cases, the chamber walls of the container pods may also be able to stack and/or couple (e.g., snap fit) together. For instance, during manufacture, when lids are not yet applied thereto, the chamber walls may fit at least partially one inside another so as to save space during manufacture of the overall container pod.

In some embodiments, a special cleaning pod having one or more cleaning agents stored therein, rather than an herbal composition, may employed. Accordingly, when a vaporizer undergoes a self-cleaning cycle, the cleaning pod may be inserted into the receptacle and the cleaning agent(s) may be released so as to clean and/or sterilize a number of the machine components (e.g., valves, channels, passageways, etc.).

As known to those of skill in the art, medical *cannabis* may be administered through a number of methods, for example, via vaporization, smoking or ingestion. While smoking is the most common method of medical *cannabis* consumption, the pharmacological response from smoking *cannabis* may be unpredictable, as the concentration of cannabinoids within each dose varies widely, depending on the manner of production. Moreover, smoking typically involves levels of heat that give rise to combustion or burning of the *cannabis*, resulting in denaturation of the cannabinoids and, ultimately, the medicinal effects. Burning of the *cannabis* may also release harmful by-products and tar, similar to that which typically arises in tobacco smoke. Such by-products may lead to respiratory problems, such as chronic bronchitis.

Vaporization, on the other hand, may allow for the therapeutic compounds to be extracted from the *cannabis*, and inhaled in a safe, predictable manner. For instance, vaporization may substantially avoid exposure to harmful by-products and their negative effects. Vaporization, in contrast with combustion, also typically contains a higher concentration of active ingredients, making vaporization generally more efficient and effective than smoking. As compared to smoke, vapor is generally lighter, more pure and less intrusive to others nearby.

Figure 9:
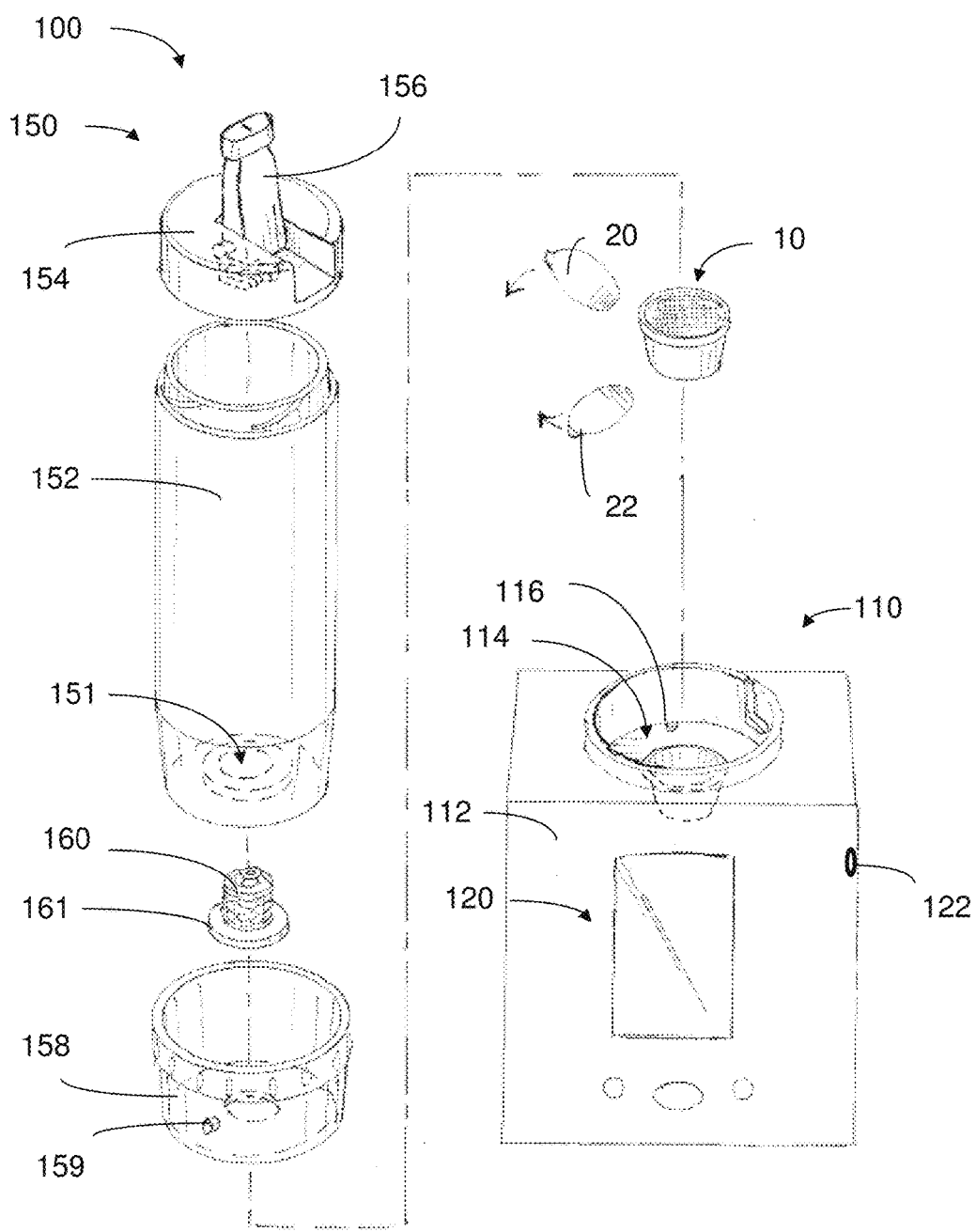
FIG. 9 illustrates an exploded perspective view of a vaporizer and a container system in accordance with an embodiment.

FIG. 9 depicts an exploded view of a vaporizer 100, similar to that shown in FIG. 1, for producing a desirable herbal vapor from the herbal composition located within the container 10. As discussed above, the vaporizer 100 may be suited to receive an optional canister 150, for storing the herbal vapor.

In some cases, the canister 150 may provide for a more discreet manner in which herbal vapor may be carried, for example, rather than a comparatively more conspicuous bag of vapor. The canister 150 may have any appropriate structure, for example, similar to that of a travel cup, thermos, etc., and which may interface with the vaporizer. As described herein, the canister 150 may or may not include an expandable balloon or bag, for further containing the herbal vapor. In some embodiments, the canister 150 sits within a receptacle of the vaporizer and is connected or otherwise coupled to the container pod, for collection of the vapor. It can be appreciated that other methods of collection may be used, as canisters and/or bags are not required aspects of the present disclosure.

The system may provide a user with an appropriate notification (e.g., audio/visual/tactile signal(s)) as the production of vapor is ongoing, or completed. In some embodiments, a sensor (e.g., coupled with the vaporizer, canister, etc.) that tracks the progress of vapor production may be employed so as to present the user with a real-time status report of the vapor being generated, or even if the vapor is being generated at all. For example, such a report may be an indicator for how full the canister or other collection apparatus is, the particular concentration of one or more cannabinoids within the vapor, whether the vaporization cycle has been completed, the existence of herbal vapor produced, amongst other information. Hence, at an appropriate time (e.g., when the canister is full of vapor, when the user wants to stop the cycle, etc.), the canister may be removed from the vaporizer and the user may sip and/or breathe the vapor through a suitable mouthpiece. The canister 150 further includes a balloon 160 configured to be coupled between the housing 152 and the lower cap 158. In this embodiment, the housing 152 includes an opening 151 appropriately shaped for receiving the unfilled balloon 160. The lower cap 158 is further configured to couple with the base 161 of the balloon 160. That is, upon assembly of the canister 150, the lower cap 158 presses up against the base 161, so that the balloon 160 protrudes through the opening 151 and into the internal volume of the housing 152. In addition, the upper cap 154 may be screwed or otherwise coupled to the housing 152, so as to provide a suitable mouthpiece 156 that channels the vapor contents stored within the bag 160 to the external environment.

As discussed herein, the container 10 may be placed within a suitable receptacle of a vaporizer 100, for producing the herbal vapor. The vaporizer may be configured to process the container and its contents so as to extract the medicinal and therapeutic compounds as fully as possible therefrom. Accordingly, the vaporizer may control the overall dosage of vapor and herbal extraction by varying a number of parameters during certain steps (e.g., decarboxylation, initial vaporization, extraction), such as cycle time, start/stop times, temperature settings, rate of air flow therethrough, relative humidity, amongst others, the combination of which may play a substantial role in producing a desirable amount of medicine and flavor.

Figure 10:
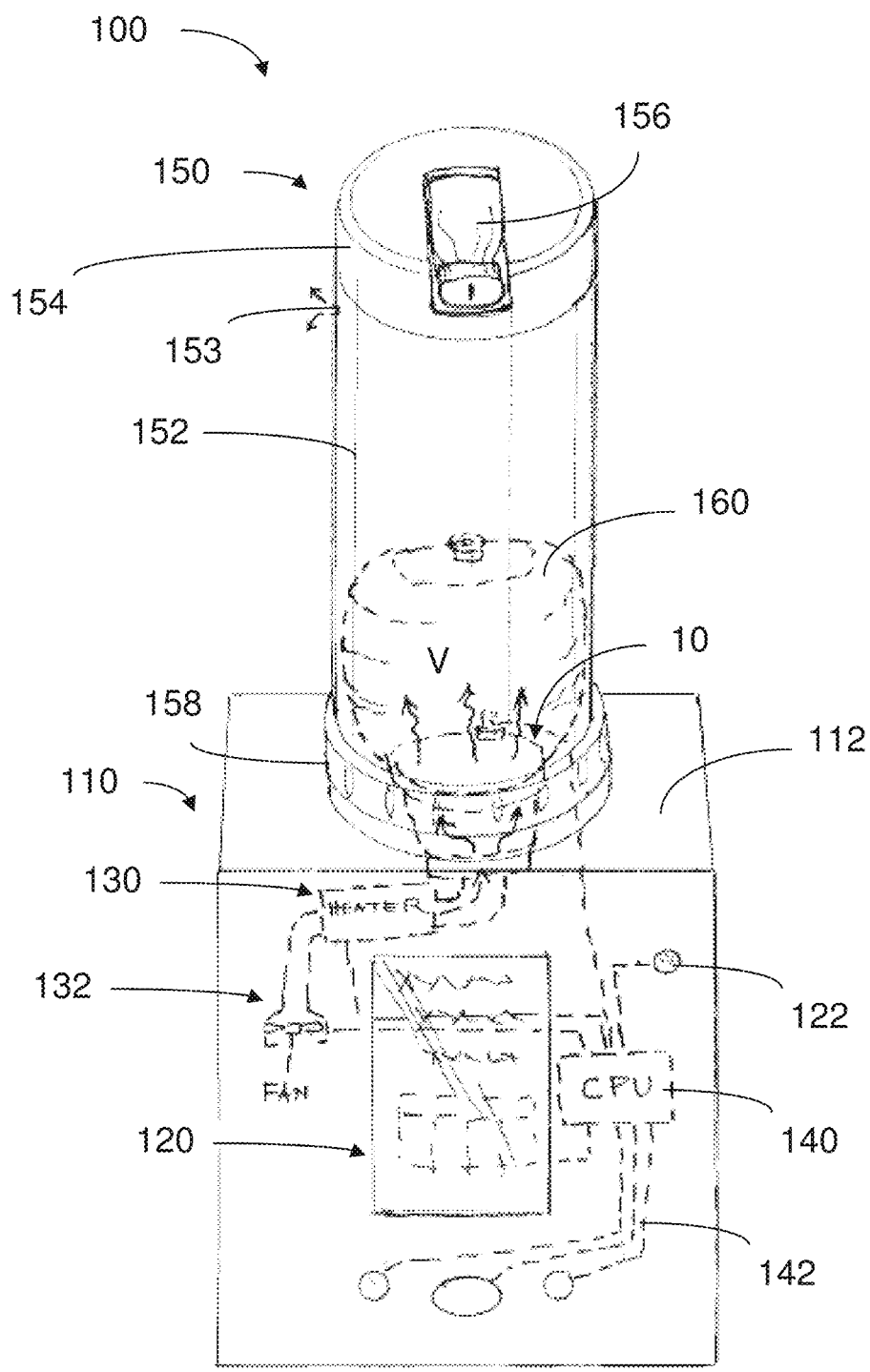
FIG. 10 depicts a perspective view showing a schematic of internal components of a vaporizer and a container system in use in accordance with an embodiment.

FIG. 10 generally illustrates a schematic embodiment of the internal working components of the vaporizer 100 while in use. The vaporizer may include a heater 130 for adjusting the temperature within the internal volume of the chamber which, in some cases, may be based on information read from the container and/or other information (e.g., patient/prescription information).

Depending on the appropriate temperature profile used to vaporize the herbal composition, the heater 130 may be configured to heat the internal volume of the chamber to a variety of temperatures between approximately 200° F. and 1000° F., or temperatures outside of this range. In some embodiments, the heater 130 may include conductive and/or radiative heating coils that generate thermal energy, which is transferred through the chamber wall and into the internal volume, where the herbal composition resides. It can be appreciated that any suitable method of heating the internal volume of the container pod may be employed. For example, the internal volume may be heated via laser, induction, convection, etc.

Alternatively, as discussed above, for some embodiments, the heater may be configured to adjust the temperature within the container via electromagnetic induction. For example, the heater 130 may include electromagnetic coils or other component(s) through which an electromotive force may be applied, for creating a magnetic field suitable to inductively heating the support member within the internal volume of the container. While not shown in this figure, one or more electromagnetic coils may be provided within the receptacle so as to surround (e.g., wrap around) the container 10 when inserted therein.

While not expressly shown in the figures, the vaporizer 100 may employ a method for distributing the contents within the container pod. In various embodiments, the receptacle 114 may be configured to oscillate, compress, spin, stir, rotate, twist, shake and/or vibrate, so as to suitably agitate and/or mix the herbal composition. For example, the receptacle may rotate the container 10 in back and forth motion to keep the contents therein distributed, freshened, moving, etc. The receptacle may also be configured to pinch the container 10 in a manner similar to that shown in FIGS. 3A-3B, yet automated. In some embodiments, the vaporizer 100 may transmit ultrasonic energy into the chamber, for distributing its contents.

As further shown in FIG. 10, the vaporizer 100 may include a pump 132 for causing air to flow through the internal volume of the chamber, and for further moving vapor produced from the herbal composition into collection region (e.g., canister, balloon, bag, piston, etc.). It can be appreciated that any suitable pump may be employed. In some embodiments, the pump may be a positive pressure or displacement pump (e.g., variable air compressor, rotary pump, reciprocating pump, linear-type pump, diaphragm pump, hydraulic pump, screw pump, piston pump, peristaltic pump, etc.), or the pump may be a vacuum (negative pressure) pump.

Though, for some embodiments, as discussed further below, the vaporizer may not require a pump. For example, a user may manually blow and/or inhale through a mouthpiece so as to engender suitable air flow through the internal volume of the chamber. In some cases, the air flow generated by the user may be adjusted depending on the particular recipe called for by the contents of the container pod.

For instance, the vaporizer 100 may include a control unit 140 having connections 142 configured for controlling a heater 130, a pump 132, air flow passageways, valves and/or other components not expressly shown, to provide a treatment protocol or recipe in vaporizing and extracting the herbal composition and produce a therapeutic vapor. In some embodiments, such a control system may give rise to an automated series of adjustments in temperature, vibration, air flow, relative humidity, cycle times within the internal volume of the chamber during herbal vaporization and extraction.

As provided herein, based on the contents of the herbal composition within the container, the vaporizer 100 may create a particular set of conditions (e.g., temperature profile, time cycle, relative humidity, level of agitation, air flow through the container, etc.), which may suitably vary over time, that result in an herbal vapor that exhibits substantially therapeutic and/or desirable qualities than would otherwise be the case. By contrast, conventional systems typically require a user to set the vaporizer to reach a certain temperature which is held for a prolonged period of time, until vaporization is complete. However, such a method of vaporization limits the extraction potential of the herbal composition. That is, without an appropriate set of conditions (e.g., via a vaporization recipe) under which the herbal composition is exposed, the potential of therapeutic/medicinal qualities that may otherwise be available from the composition may be under-utilized. In fact, conventional methods of herbal vaporization often results in combustion, burning off and/or denaturation of the more desirable chemical compounds. In some cases, such a recipe is input to the control unit 140 of the vaporizer based, at least in part, on the information read from the container. Or, the recipe may be manually input to the control unit 140 via the user interface 120.

FIG. 10 also shows that as air is pumped through the system according to an appropriate recipe, a suitable herbal vapor V is collected into the balloon 160, as depicted by the waved arrows. Accordingly, the balloon 160 expands into the internal volume of the housing 152. As the balloon 160 expands into this space, ambient air displaced from the internal volume of the housing 152 exits through a vent 153.

In some embodiments, as the balloon 160 is suitably filled with vapor, the interface 120 may provide the user with an appropriate indication of the status of vaporization. For example, the interface 120 may provide an indication that the overall vaporization process is completed, or an indication of how much vapor has been collected, or what type and/or quality of vapor has been collected.

Figure 11:
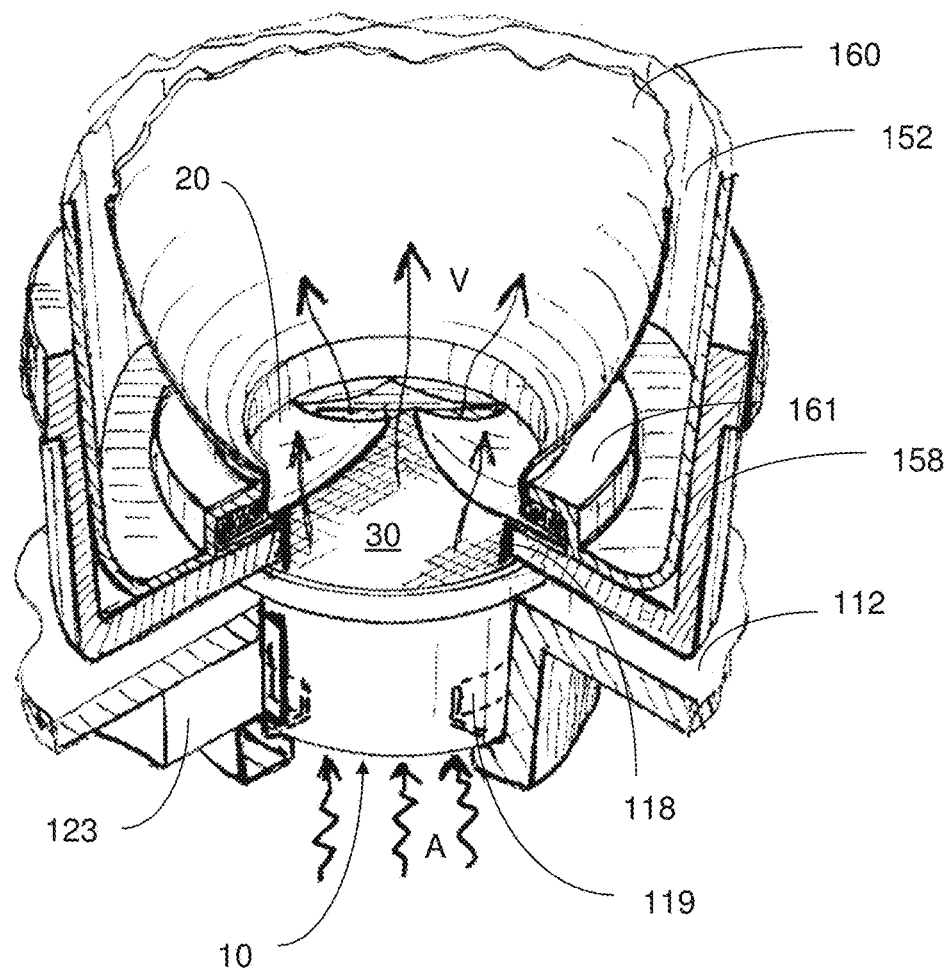
FIG. 11 shows a close up cut-away perspective view of a vaporizer and a container system in use in accordance with an embodiment.

FIG. 11 depicts a close up of the process of vapor production within the vaporizer 100. As further shown, for some embodiments, the receptacle of the vaporizer includes sharp edges 118, 119, for puncturing the respective lids 20, 22 of the container and, hence, releasing the seal of the container from both upper and lower sides.

As an example, upon insertion of the container 10 into the receptacle, the lower sharp edge 119 may be exposed and protrude upward so as to pierce the lower lid 22 and break the seal of the container 10 from the bottom. This opening allows air to flow into the internal volume of the chamber, for example, from a pump or other suitable channel for air flow.

In accordance with FIG. 9, the canister 150 may then be placed overtop the container 10 held within the receptacle 114. In some embodiments, the upper sharp edge 118 may protrude downward from the base 161 of the balloon so as to puncture the upper lid 20 and provide an opening into the container 10. This opening allows air to flow out from the internal volume of the chamber and into the canister or other collection region.

Accordingly, as shown in FIG. 11, air A (depicted by the waved arrows) may flow (e.g., pumped, blown, inhaled, etc.) from the lower side of the container and into the internal volume. The air flows through the internal volume and carries vaporized, nebulized and/or otherwise extracted herbal ingredients outward from the internal volume and out as vapor V (depicted by the solid arrows), for collection into the balloon 160.

It can be appreciated that the container can be opened by any suitable manner. In some embodiments, as discussed herein, the container may be punctured by sharp, knife-like edges upon suitable placement into the receptacle of the vaporizer. The sharp edges may extend around the perimeter of the container lids, as shown in FIG. 11. Or, the sharp edges may extend across the surface one or more of the lids, resulting in the lid(s) being cut into flaps. In some cases, the sharp edge, or other component of the vaporizer, may be twisted, actuated or otherwise moved so as to remove or reposition the lid(s) in a manner that does not substantially obstruct passage of air into or out from the container.

Figure 12:
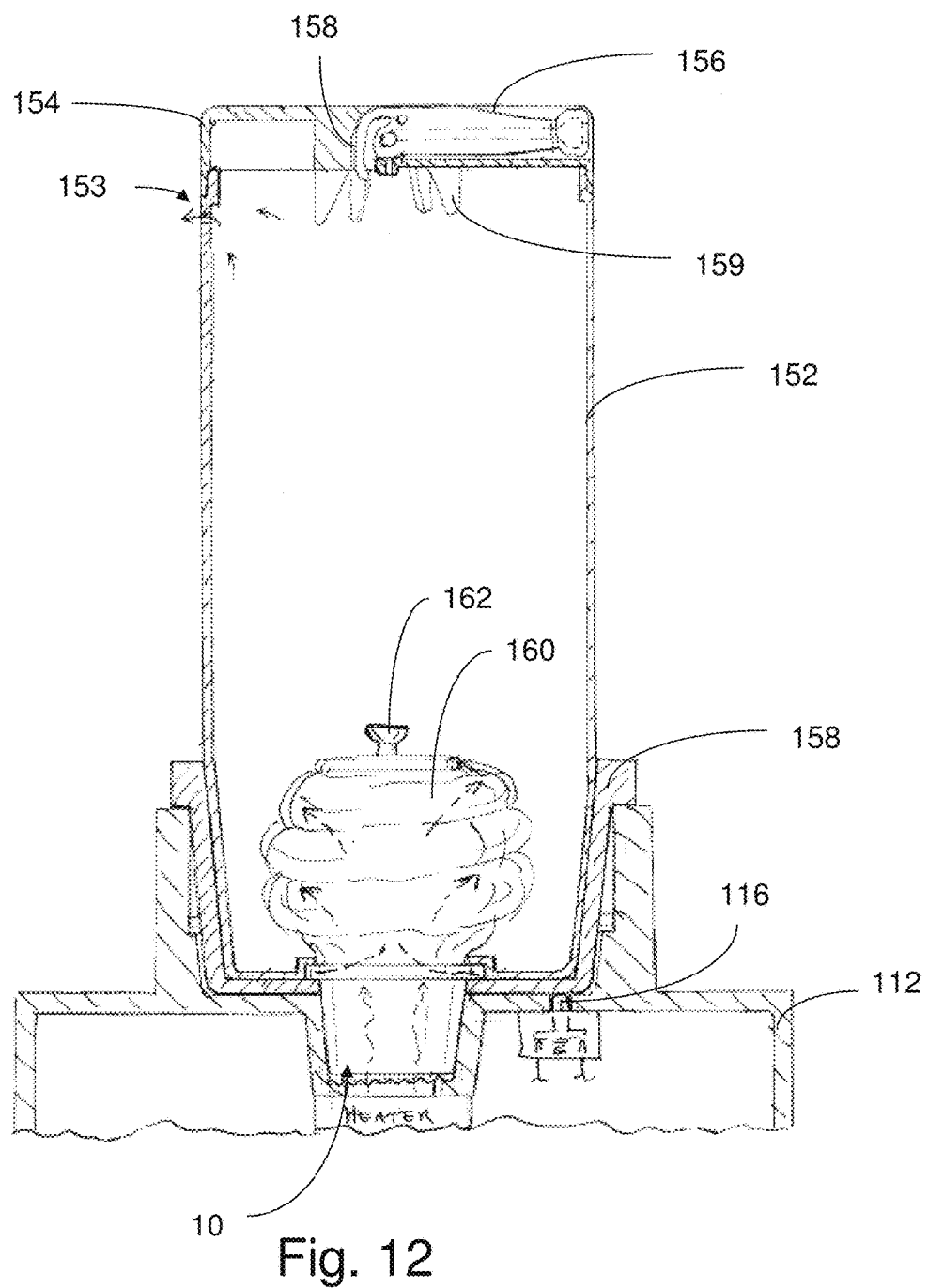
FIG. 12 illustrates a cross-section view of a vaporizer and a container system in use in accordance with an embodiment.

FIG. 12 shows an illustrative embodiment during operation of the vaporizer where the balloon 160 collects herbal vapor arising from the container 10. That is, vapor produced from the heated internal volume of the container 10 flows (depicted by the dashed arrows) into the balloon 160, which consequently expands into the space enclosed by the container. It can be appreciated that other arrangements for collecting the herbal vapor may be provided. That is, collection of the herbal vapor does not require a balloon and canister arrangement as depicted. For example, it may be possible for the herbal vapor to be collected into an otherwise empty canister without a balloon or bag. Or, the herbal vapor may be collected into a more rigid bellows or piston-like structure (e.g., similar to that of an accordion) that expands or contracts based on the flow of air into or out of the structure. In some embodiments, once suitably filled, the canister 150 may be removed from the base 110 of the vaporizer 100, to be consumed at a later time.

Figure 13A:
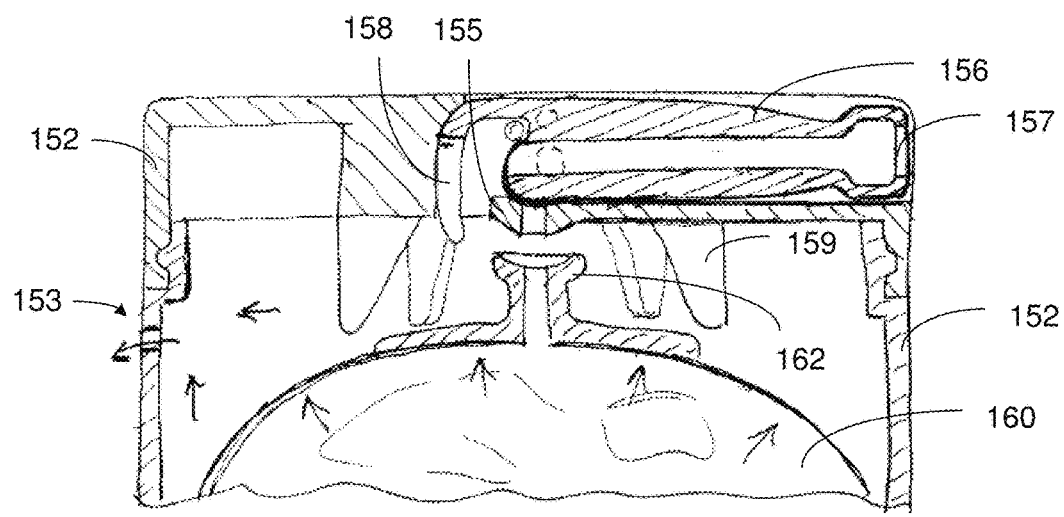
FIGS. 13A-13B depict a cross-sectional view of a vaporizer and mouthpiece coupling in accordance with an embodiment.
Figure 13B:
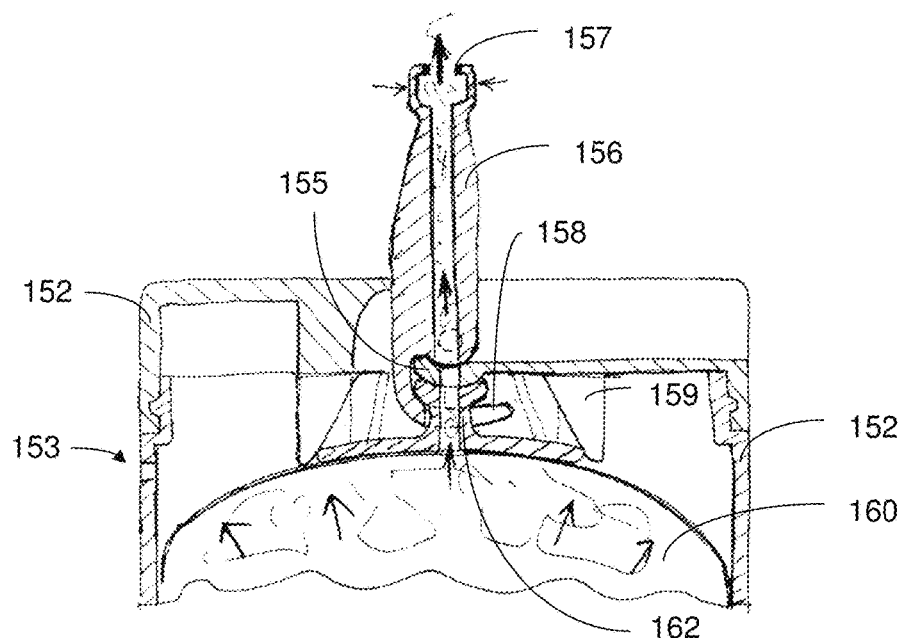

FIGS. 13A-13B depict a closer view of the balloon 160 and mouthpiece 156 interface as a suitable connection is made therebetween. FIG. 13A shows expansion of the balloon 160 as it approaches the mouthpiece 156, and as air exits through the vent 153. As further shown in this embodiment, the balloon 160 includes a connection member 162 that has a valve arrangement which allows the herbal vapor to exit from the balloon when desired, and the mouthpiece 156 includes a corresponding connection member 155 that provides a conduit through which vapor may pass through toward the exit of the mouthpiece 156.

For example, while the balloon 160 expands within the container, the connection member 162 may have a valve that prevents air or vapor from exiting the balloon 160, at least, until a suitable coupling is established with the corresponding connection member 155 of the mouthpiece 156. An upper end of the canister 150 may include support guides 159 that are shaped or otherwise configured to position and/or guide the connection member 162 of the balloon toward the corresponding connection member 155 of the mouthpiece. In FIG. 13A, the mouthpiece 156 resides in a disconnected (shown in this embodiment to be horizontal)

position, which cuts off the passageway between the balloon 160 and the mouthpiece end 157, preventing the vapor from exiting the canister 150.

Once the respective connection members 155, 162 are appropriately coupled, vapor stored within the balloon 160 may be allowed to pass through toward the end 157 of the mouthpiece 156, for consumption. FIG. 13B depicts an illustrative embodiment of the mouthpiece 156 in an orientation that permits vapor located within the balloon 160 to pass therethrough and outward into the external environment. As shown, the support guides 159 position the corresponding connection members 155, 162 against one another, so as to provide a passage for the vapor therethrough. Here, the mouthpiece 156 is rotated from the disconnected (shown here to be horizontal) position of FIG. 13A to a connected (shown here to be vertical) position of FIG. 13B, providing a suitable passageway between the balloon 160 and the mouthpiece end 157, through which vapor may travel. The connection member 162 includes an opening through which a hook 158 of the mouthpiece may be inserted, for providing a suitable degree of support when the mouthpiece 156 is placed in the connected position. It can be appreciated that other configurations of the mouthpiece and the manner in which vapor is contained and/or allowed to exit the collection region of the vaporizer may be possible.

In some embodiments, even when the mouthpiece 156 is suitably placed in the connected position where a passageway is established between the internal volume of the balloon 160 and the mouthpiece 156, the vapor may still be prevented or otherwise obstructed from exiting therefrom. For instance, the end 157 of the mouthpiece may include a septum that seals the passageway from the external environment. In certain embodiments, the septum may be configured to be opened to the outside upon application of a suitable pressure. For example, a user may bite down on the end 157 (pressure depicted by the horizontally directed solid arrows), which may cause the septum to open and allow vapor exit therefrom, as depicted by the solid arrows leading through the passageway of the mouthpiece.

Figure 14:
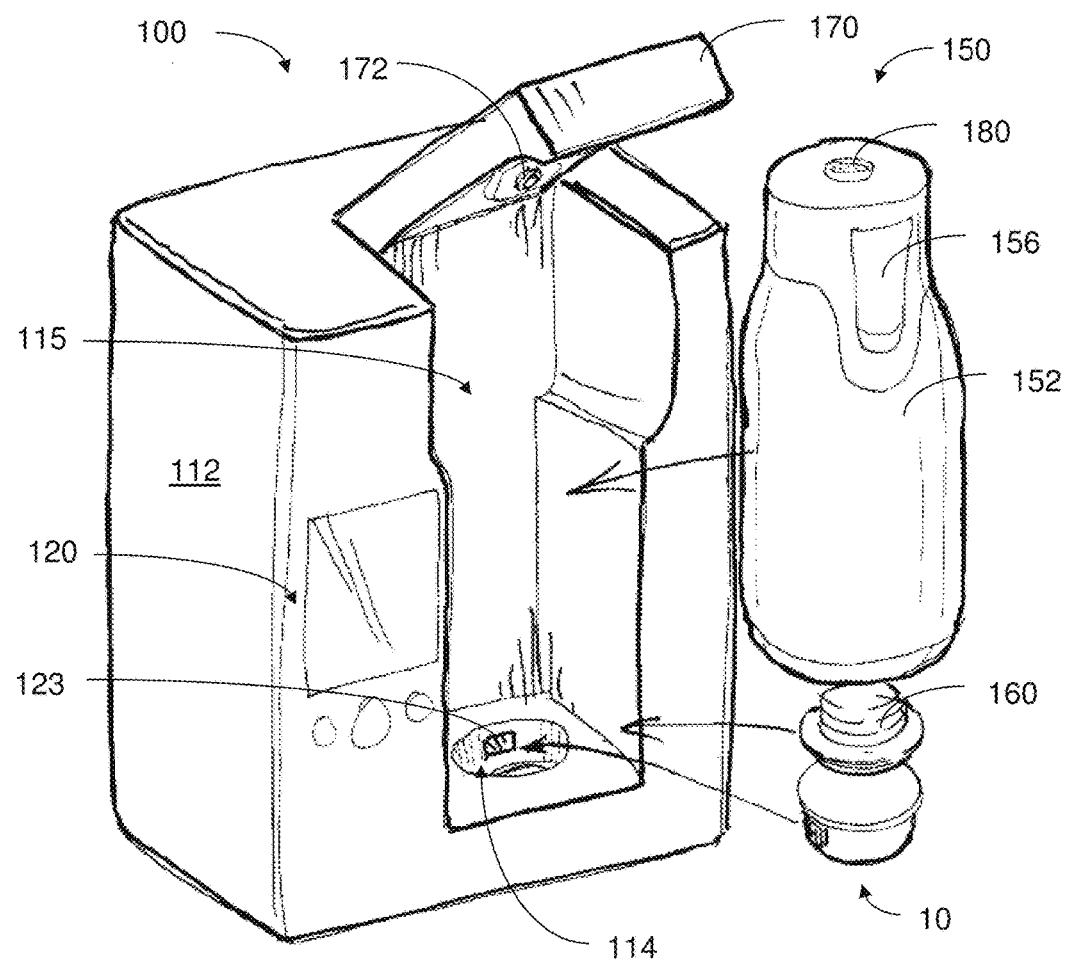
FIG. 14 shows a perspective view of a vaporizer and a container system in use in accordance with an embodiment.

FIG. 14 shows another illustrative embodiment of a vaporizer 100 including a housing 112 having a first receptacle 114 for receiving a container 10 with an herbal composition located or sealed therein, and a second receptacle 115 for receiving a canister 150, for collecting the herbal vapor produced from the container 10. Once the container 10 is appropriately situated within the first receptacle 114, the canister 150 may be placed within the second receptacle 115. As further shown in this embodiment, the receptacle 114 includes a digital reader 123 for providing relevant information about the contents of the container 10 to the control unit.

As also shown in FIG. 14, the vaporizer 100 includes a lid 170, for locking or otherwise securing the canister 150 in place. Here, the lid 170 may have a latch and may also be rotatable between unsecured and secured positions, however, it can be appreciated that any suitable configuration may be employed to keep the canister 150 in place while also providing a suitable connection with the vaporizer 100. In some cases, the canister 150 may be physically locked in place, preventing any undesirable ejection or removal of the canister 150 and/or container pod 10 during operation.

In some embodiments, the lid 170 may also include a passageway 172, which may be coupled with a corresponding passageway 180 of the canister 150, through which air and/or vapor from the canister 150 may flow. In such cases, once the canister 150 is appropriately secured within the receptacle 115, air and/or vapor from the canister may be recirculated through the vaporizer 100 and flowed back into the canister.

In some embodiments, not expressly shown in the figures, vapor may be recirculated through the system under multiple cycles or, for example, via a secondary balloon or canister, which may result in an overall more dense and/or potent vapor than would otherwise be the case. For instance, after exiting the container 10, the vapor may be caused to flow back through the container 10, extracting additional flavor and/or chemical compounds from the herbal composition.

In some embodiments, the vapor may be divided into separate collection regions/bags. For example, the vaporizer may include a diverter that directs a first portion (e.g., vapor produced over an initial period of time) to a first bag or collection region, and directs a second portion (e.g., vapor produced during another period of time) to a second bag or collection region. As further discussed herein, certain cannabinoids may have different vaporization temperatures, and so the vapor may be divided according to the particular stage or timing of vaporization. For instance, as THC has a comparatively lower vaporization point than CBD/CBN, in some cases, vapor collected during an initial stage of vaporization may have more THC than vapor collected during a later stage of vaporization.

The vaporizer may include any suitable valve arrangement for regulating air/vapor flow therethrough. For example, a one-way valve may be located between the container pod and the collection region (e.g., balloon, bag, canister), so that vapor is unable to flow back out from the collection region. Such a valve may be placed in an open or closed position, as desired, according to the particular vaporization process.

In some embodiments, the vaporizer may have one or more air filters that are configured to keep odors around the vaporizer under control. For example, ozone technology may be employed to eliminate or otherwise reduce odors within the vapor and outside the system. In some cases, certain air freshening liquids/solids and/or other agents may be used to add new flavors, or alternatively mask vapor odors.

Figure 15:
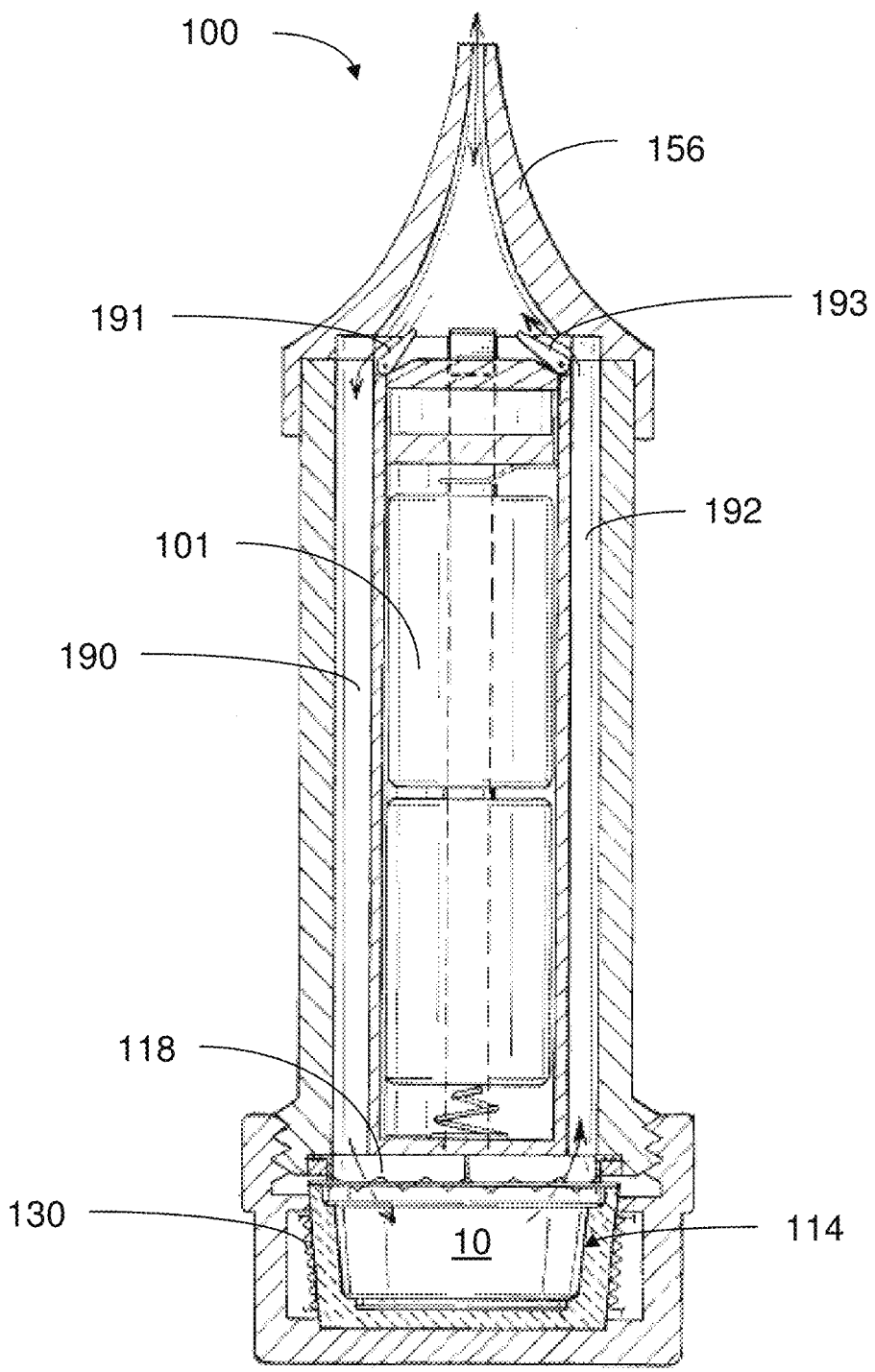
FIG. 15 depicts a cross-sectional view of a vaporizer in accordance with an embodiment.

In some embodiments, the vaporizer 100 may be portable in nature. For example, the vaporizer 100 may be battery-powered and/or may be compact enough for user carry-along. FIG. 15 depicts an illustrative embodiment of a portable vaporizer 100 having a receptacle 114 within which a container 10 including a suitable herbal composition is inserted. The receptacle 114 includes a sharp edge 118 for puncturing the container 10 upon appropriate insertion, and allowing air flow therethrough. The vaporizer 100 may include a heater 130 (e.g., convective, induction coils, etc.) for adjusting the temperature of the herbal composition held within the internal volume of the container 10. In some embodiments, the vaporizer 100 includes a pump (not shown in this figure) for forcing air flow through the internal volume of the container, however, for certain embodiments, a pump is not required.

As further shown in FIG. 15, the vaporizer includes space for batteries 101 to reside, allowing for portability of the vaporizer. Though, other methods for powering the vaporizer may be possible, such as by incorporating a number of solar panels, a mechanical generator (e.g., hand-powered generator/crank), etc.

The vaporizer 100 may incorporate a canister, bag or other type of collection region directly therein. That is, the vaporizer 100 may be portable, yet may also be able to store vapor for a user to carry along and consume as desired. Accordingly, a portable vaporizer may be able to receive a container pod and process its herbal contents to produce a desirable herbal vapor that is stored within the vaporizer itself, rather than having to be separated therefrom.

As further shown, in this embodiment, channels 190, 192 provide passageways through which air may flow. For example, air blown into the mouthpiece may move past an entry valve 191 (e.g., motor or spring controlled flap) through channel 190 and into the internal volume of the pod chamber. In some embodiments, air blown into the mouthpiece may travel to the herbal composition within the container pod and, when coupled with a suitable amount of heat, may provide a decarboxylating function (i.e., converting THC-acid into THC). Further, as the vaporizer parameters are adjusted to subject the herbal composition within the internal volume to vaporization and extraction, the air circulates and collects herbal vapor, which eventually flows out through channel 192, past an exit valve 193 (e.g., another motor or spring controlled flap) and back out the mouthpiece for consumption. However, it can be appreciated that air may be circulated throughout the vaporizer in any other suitable manner.

In certain instances, a user may provide air flow through the internal volume of the container. For example, the user may blow into and/or inhale from the mouthpiece 156 to create air flow through the vaporizer 100. The air flow generated by the user may flow through the internal volume of the container and carry the herbal vapor back out through the mouthpiece. Such a vaporizer 100 may also include a control unit that senses the degree of air flow provided by the user, and then adjusts the rate of air flow through the container and other areas of the vaporizer based on a preferred recipe for producing a desired herbal vapor.

The vaporizer may include one or more sensors for sensing information regarding the container pod and/or collection region, and providing the control unit with this information. In some embodiments, the sensor(s) may sense the temperature, rate of air flow and/or relative humidity within the internal volume of the pod chamber. For example, the sensor(s) may include one or more appropriate thermocouples, moisture/humidity sensors, air flow meters, light sensors, valves, etc., located within the internal volume of the pod chamber and/or around the chamber.

Based on this sensed information (e.g., temperature, relative humidity, light, air flow, etc.), the system may be able to determine the potency, dryness, and other related factors that contribute to herbal extraction. So, in accordance with the preferred recipe under which the herbal composition is to be processed, the heat applied to the pod chamber, humidity and/or rate of air flow therethrough may be suitably adjusted. In some instances, the amount of heat applied to the pod chamber may affect the overall temperature as well as relative humidity within the internal volume. The construction of the pod chamber (e.g., insulation, ability to absorb moisture, etc.) may also contribute to the conditions under which the herbal composition is subjected. Or, based on the sensed information, other appropriate parameters may be adjusted.

In some cases, the relative humidity within the pod chamber may affect the overall quality and consistency of the herbal vapor. Hence, for some embodiments, the system may be configured to monitor and maintain the relative humidity (e.g., approximately 60-62%) within the internal volume of the pod during operation.

In some embodiments, the herbal composition itself may be measured and dried (e.g., through heating) so as to reach a baseline moisture (e.g., approximately 8-10%) that may be substantially maintained and, in some cases, preferable for vaporization of ingredients within the pod. This moisture content may be maintained via a suitable feedback mechanism, recirculation, and/or any other suitable method in accordance with the present disclosure.

In some embodiments, the vaporizer employs a feedback mechanism (e.g., via a Wheatstone bridge configuration) that controls the temperature, relative humidity and/or air flow through the internal volume of the pod chamber. In some cases, it may be possible to test the electrical impedance/resistance of the container pod, or contents therein, to provide information regarding its properties. For instance, electrical leads may be attached directly to the container pod (e.g., on opposite sides), which may allow for the resistance across the container pod to be determined. This resistance may provide a user/system with information regarding the temperature, humidity, air flow, etc. within the pod. As discussed above, in conjunction with the temperature and relative humidity within the pod chamber, the rate of air flow may be also be suitably regulated.

In some embodiments, a reed valve may be used to as a one-way valve, mechanically or electrically actuated, that is adapted to open or close depending on the pressure drop across the valve and/or based on a user input via an interface. Such a valve may also provide an indication of the rate of air flow at various locations of the system.

In some cases, the valve, or suitable component(s) coupled thereto, may provide feedback (e.g., audio, visual, tactile, electronic, etc.) as to the preferred blowing or inhalation speed/force, for producing a desired herbal vapor. For instance, when a user blows into or inhales from the mouthpiece, the valve arrangement may be configured to open when the air pressure is sufficiently high and/or provide a signal (e.g., audio signal due to reed vibration, beeping sound from a computer, visual indication from a LED or other light source, etc.) that the level of air flow is adequate for suitable vaporization of the herbal composition. The valve may then change from a closed position to an open position, or the user/system may generate a signal that causes the valve to open, allowing vaporization to occur. In some cases, the valve may remain closed if the air pressure does not reach a threshold value.

In some embodiments, the vaporizer may be constructed as a musical instrument. For example, the reed valve may not only provide feedback regarding the level of air pressure within the vaporizer, but may also allow a user to play musical notes therewith. Accordingly, while not expressly shown in the figures, the vaporizer may be structured (e.g., with appropriate channels, finger holes, etc.) as a musical wind instrument.

In some embodiments, upon continued use, the vaporizer may be calibrated (automatically or manually) according to the manner in which a user blows or inhales. For example, the user may not be inclined to blow and/or inhale in the mouthpiece of the vaporizer to a significant degree. Hence, it may be preferable for other parameters of the vaporizer to be adjusted accordingly to compensate for any lack of air flow. For instance, the temperature or humidity within the pod chamber may be raised, lowered or otherwise adjusted so that at least the same amount of flavor and potency of herbal vapor is produced as would be if the air pressure were as originally specified by the recipe. Or, the vaporizer may include a relatively small pump that appropriately compensates for any deficiency in pressure generated at the mouthpiece by a user.

In some cases, the vaporizer may be configured as a smart machine that learns the preferences of a user. For example, a user may input a number of parameters and/or the vaporizer may track the particular conditions for vaporizing the contents of a number of container pods. The user may determine that a certain set of conditions may be especially effective in producing an herbal vapor that achieves a favorable experience. The vaporizer may also track specific combinations of container pods and vaporization conditions that correspond to favorable user experiences, and may communicate such combinations to the user for later use, as suitably desired.

As discussed above, the vaporizer may include a suitable interface through which a user may input commands into the vaporizer, for controlling various components (e.g., heater, pump, etc.) as well as receive information regarding the vaporization process. FIGS. 16A-16I illustrate screen shots of an exemplary display interface for a vaporizer. It can be appreciate that the interface may employ any suitable flow process, as the present disclosure is not so limited.

Figure 16A:
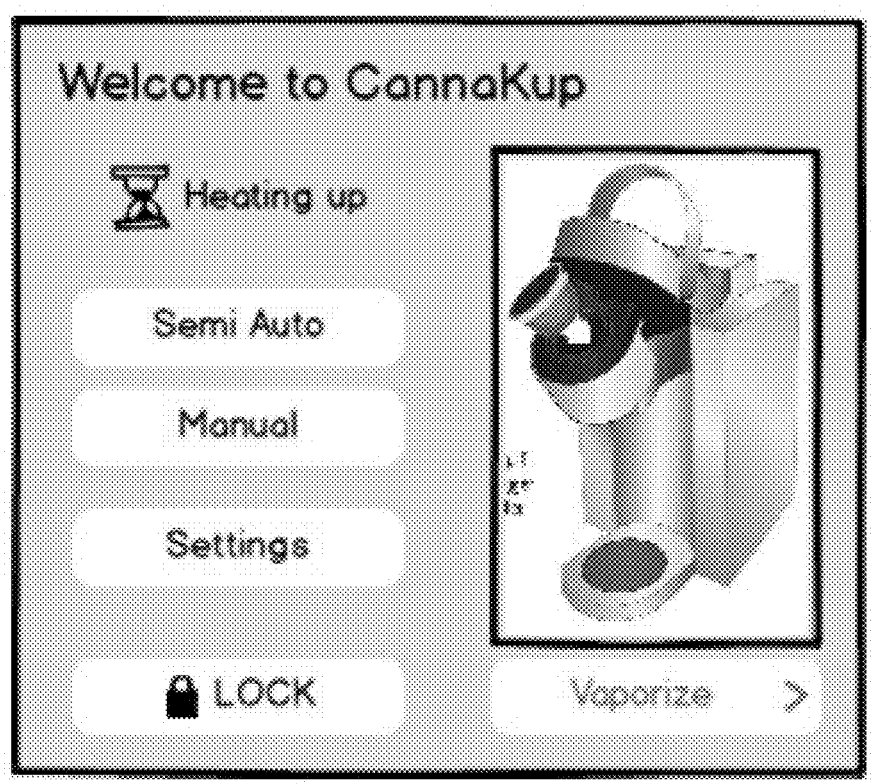
FIGS. 16A-16I illustrate screen shots of a display interface for a vaporizer in accordance with an embodiment.

FIG. 16A shows an introduction screen 300 that welcomes and invites the user to select one or more options while the system warms up. When the "Semi Auto" mode is selected, the system is configured to process a container pod carrying a suitable herbal composition according to a pre-specified recipe, for example, having particular temperature, humidity, flow rate profiles over time. In some cases, this recipe is provided based on the particular container pod that is loaded into receptacle. For example, as discussed above, a digital reader of the vaporizer may read markings (e.g., barcode, QR code, instructions, ingredients, etc.) on the external surface of the container and an appropriate recipe tailored for the herbal contents within the pod may be loaded in. Of course, a user may manually override particular aspects of the recipe as desired. For example, the user may want to heat the herbal composition at a higher temperature, or for a longer period of time, in which case the adjusted parameters may be specified. When the "Manual" mode is selected, the system allows the user to configure or program the vaporizer to process the container pod, as desired, without the benefit of a predetermined recipe. When "Settings" is selected, the user is able to modify any appropriate features of the system, for example, display settings, language, wireless connectivity, lock features, enable logging, etc. However, before any of these options are accessed, the user may be required to unlock the system.

Figure 16B:
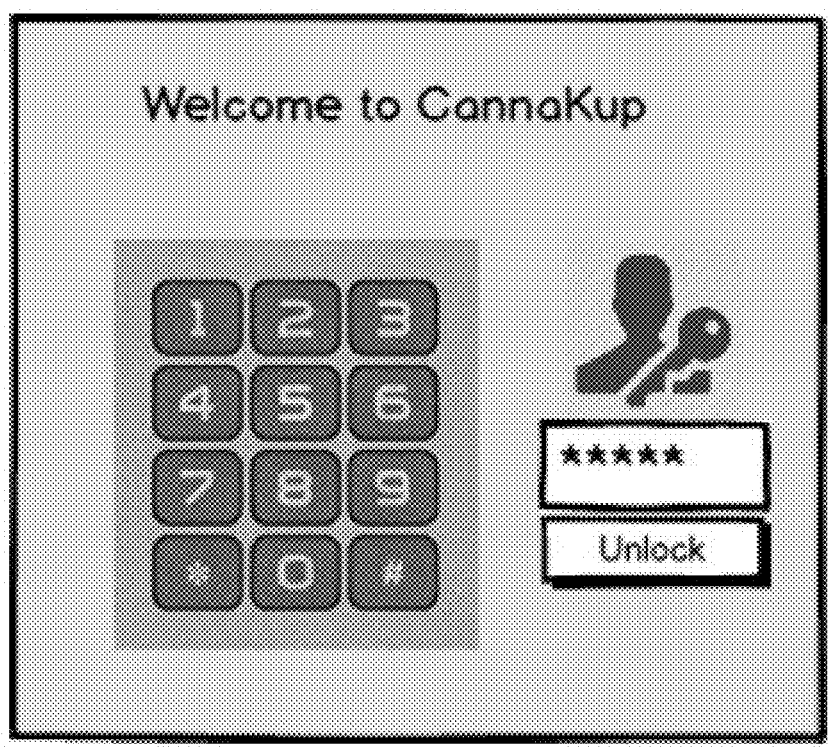

FIG. 16B shows an authorization screen 302 that requires a user to enter in an identification and passcode which, when entered properly according to an authorized identification pattern, allows the user access to the system. Such a feature may provide the system with a suitable level of safety so that only authorized persons may be able to use and consume the herbal vapor produced from the system. In some embodiments, the authorized identification pattern is provided from the information read from the surface of the container and, hence, the passcode is required to match this pattern. If the container pod has already been used, it may be preferable for the system to prevent a user from such reuse. For instance, it may be unsafe and/or undesirable for a partially used, or improperly refilled, pod to be subject to conditions that are intended for a different type of pod, and herbal composition stored therein.

It can be appreciated that any appropriate method of authentication may be used. In some cases, the vaporizer may be programmed so as to be deactivated or locked out from further use until a particular time has been reached. In some embodiments, biometrics that identify individuals based on human characteristics may be used to authenticate a user, for example, analyses based on fingerprints, retina, breath, hand geometry, odor, facial recognition, DNA, amongst others. It may be also preferable for the system to incorporate suitable child safety features, as may be apparent to those skilled in the art. Thus, the vaporizer may incorporate a series of safety features that allow for the appropriate person(s) to be using the system at the appropriate time.

Figure 16C:
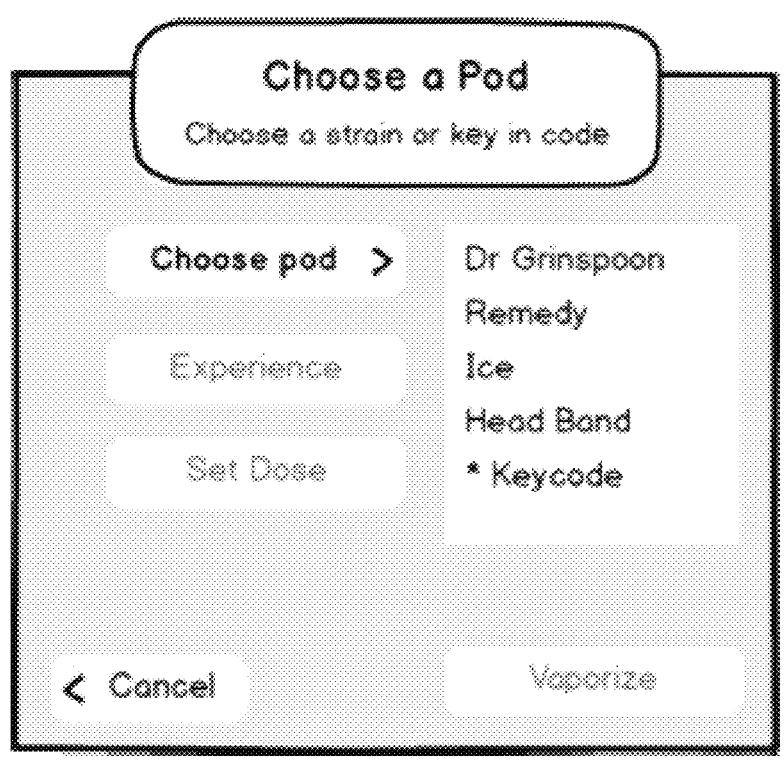

As shown in FIG. 16C, after the vaporizer has been authorized for use, the interface may provide a selection screen 304, which prompts the user to select from a number of options within separate categories. In this embodiment, the categories from which the user is prompted to select include the type of pod, type of experience and type of dose. As the screen prompts the user to "Choose pod," a number of options, which may or may not require their own authorization code for access thereof, may be presented for selection by the user.

Figure 16D:
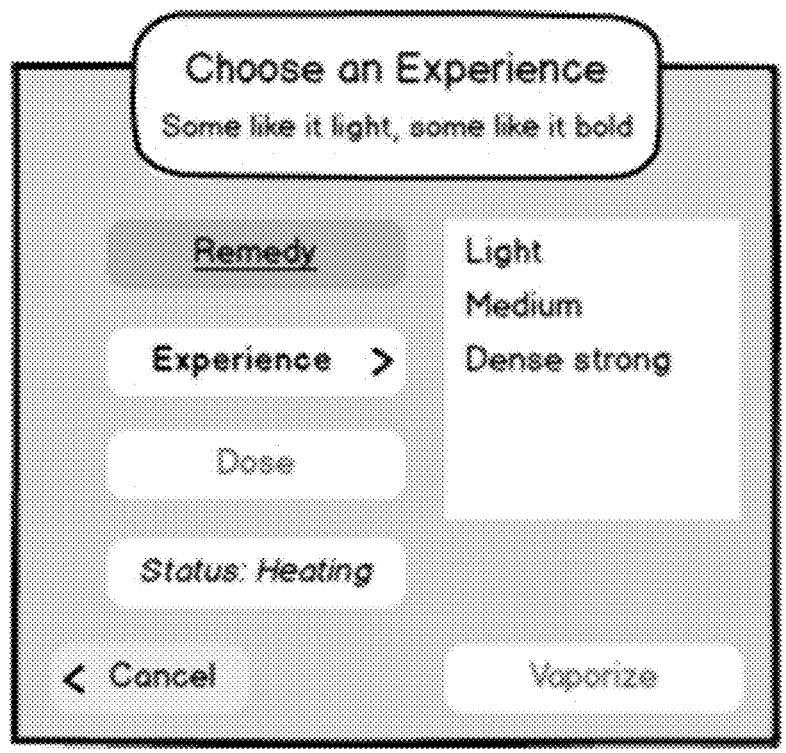

In this particular example, as shown in FIG. 16D, the "Remedy" pod option is selected. Accordingly, relevant information regarding the "Remedy" pod (e.g., strain, ingredients, percentage(s) of certain chemical compounds present, package date, weight, etc.) is loaded into system memory, which is pertinent in determining which vaporization process recipe is employed. That is, depending on the specific ingredients of the herbal composition, the vaporization recipe will vary.

Upon selecting the type of pod, the selection screen 306 then prompts the user to select an experience from the "Experience" category. Hence, a number of options, which may or may not require an authorization code, may be presented for selection thereof.

Figure 16E:

In this example, as shown in FIG. 16E, the "Medium" experience option is selected. As a result, the vaporizer may employ a recipe that gives rise to a corresponding level of experience. For example, if the desired level of experience is "Light," then the vaporizer may call for a recipe that produces a relatively thin or dilute amount of herbal vapor. For example, the rate of air flow through the internal volume may be comparatively fast. In contrast, when a "Dense strong" experience is selected, a recipe that produces a fairly thick or dense amount of herbal vapor may be employed. For instance, air flow through the pod chamber may be slow, so that chemical compounds are more readily able to accumulate.

Figure 16F:
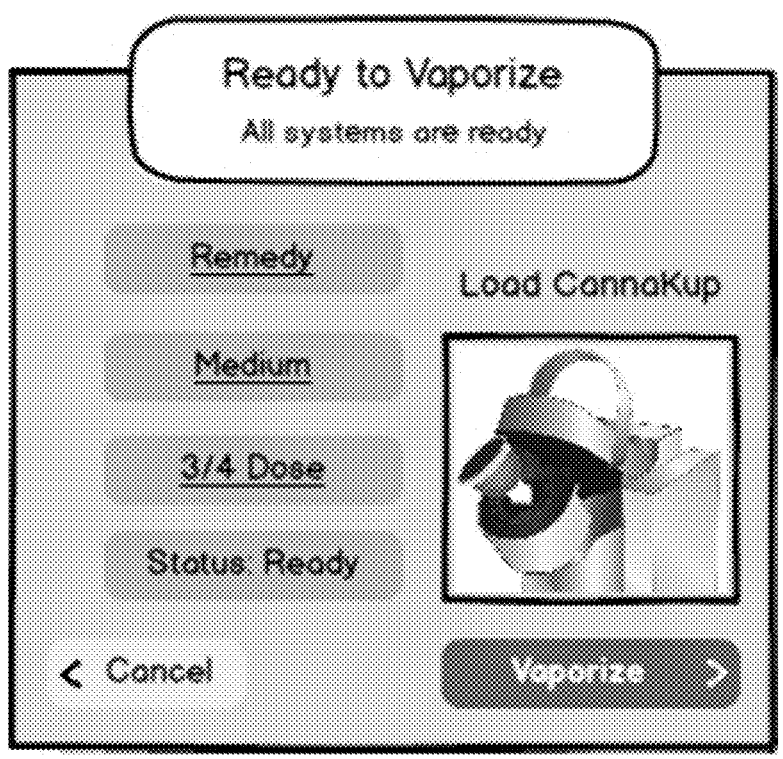

After the type of experience is chosen, the selection screen 308 subsequently prompts the user to select a dose from "Dose" category. Here, as shown in FIG. 16F, the "¾ dose" option is selected. The recipe followed by the vaporizer is then adjusted accordingly. As an example, if the desired dosage level is a "Full dose," then the time of vaporization may extended so as to collect a full amount of herbal vapor, for example, into a canister or bag. Or, if the desired dosage level is a "¼ dose," then the time of vaporization may be shortened appropriately such that only ¼ of a full dose is ultimately collected. In this example, the selected "¾ dose" may call for a vaporization time period in between that employed for a "Full dose" and a "½ dose."

The conditions (e.g., amount of time, rate of flow, temperature, humidity, etc.) for each vaporization cycle may depend on the amount and concentration of ingredients within the herbal composition. For example, a concentrated strain of *cannabis* having relatively high amounts of certain medical and/or psychoactive compound(s) may require a shorter period of time and/or a less amount of heat to achieve a high dosage in comparison to a less concentrated strain having less of the medical/psychoactive compound(s). The ability for the system to monitor and tailor dosage offers doctors and patients the ability to control administration of the herbal vapor safely and securely. By contrast, conventional systems rely on the patient's ability, or lack thereof, to manually adjust each of the conditions under which the herbal composition is exposed.

It can be appreciated that the particular recipe selected and executed by the vaporizer may depend, at least in part, on each of the categories chosen by the user. For instance, depending on each of the container pod selected, the desired experience and dosage, the vaporization recipe may be tailored accordingly.

As further shown in FIG. 16F, once selections are made for each of the three categories, the system is then ready for vaporization. Accordingly, the user is able to select "Vaporize."

Figure 16G:
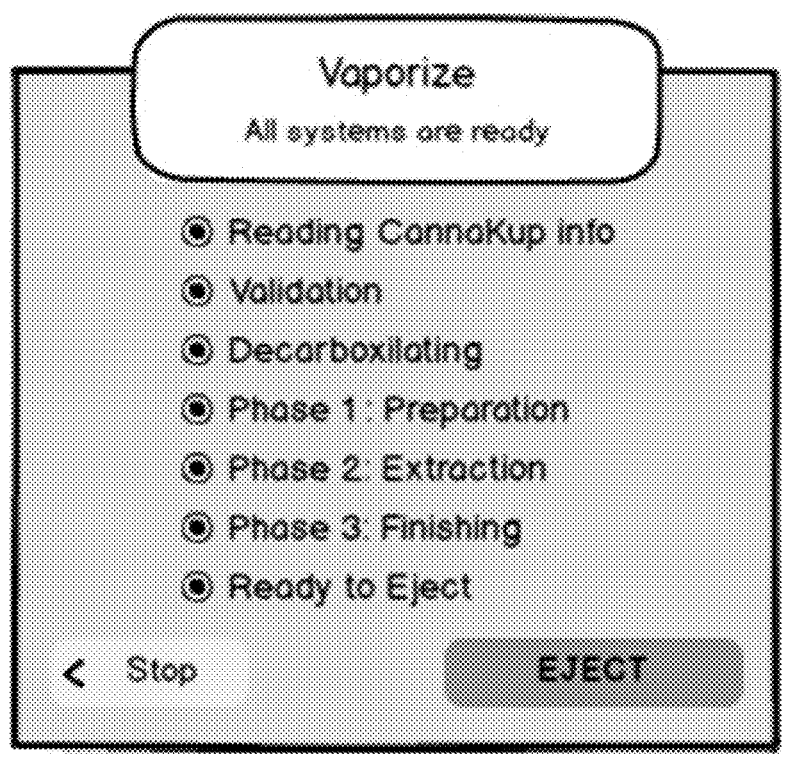

FIG. 16G then shows an example of a vaporization screen 312, which provides a display that indicates the stage of vaporization that is ongoing as the vaporizer automatically adjusts the conditions within the pod according to a recipe tailored to produce a desired dosage of herbal vapor based on the particular herbal composition and patient need(s). As further shown, before vaporization begins, the vaporizer collects and validates relevant information regarding the contents within the pod, for example, by reading markings on the external surface of the container, ensuring that the user is authorized to consume the vapor produced from this particular container pod, by having relevant information input into the system via the user interface, or undergoing any other suitable validation process.

Once the pertinent information is collected and validated, the vaporizer may begin the process of producing the herbal vapor. In some embodiments, suitable production of the herbal vapor may involve a number of stages, for example, decarboxylation, initial vaporization and extraction. Decarboxylation of the herbal composition may occur during processing of the container pod within the vaporizer, though in some cases, decarboxylation of the herbal composition may actually begin as early as during preparation of the herbal composition for storage within the container pod. That is, even before the container pod is placed within the receptacle of the vaporizer, the process of decarboxylation may have already initiated.

In the context of *cannabis* vaporization, as known to those skilled in the art, decarboxylation involves the conversion of THC-acid to THC. Raw *cannabis* contains a substantial amount of THC-acid, which is not psychoactive. That is, THC-acid does not alter brain function with respect to perception, mood, consciousness, or other psychological states. However, when a carboxyl group is removed from THC-acid (e.g., in the form of water vapor and carbon dioxide), THC is formed, which is a psychoactive compound. In general, decarboxylation of *cannabis* involves converting THC-acid to THC with minimal or otherwise low levels of vaporization of cannabinoids, terpenes and flavonoids within the *cannabis*. Similar to curing, the process of decarboxylation may begin once the *cannabis* is cut from the stem. Though, in some instance, decarboxylation can be accelerated upon suitable heating of the *cannabis*.

In some embodiments, lower decarboxylation temperatures involve longer processing times, yet less loss of terpenes due to vaporization. Heating of the *cannabis* within an enclosed environment may also help to reduce the loss of cannabinoids, terpenes and flavonoids by trapping or containing vapor and allowing it to be reabsorbed into the *cannabis*, or other herbal material, as it slowly cools down after decarboxylation.

Those of skill in the art may appreciate that the vaporization points of major cannabinoids, terpenes and flavonoids range between approximately 245° F. and approximately 480° F. Accordingly, suitable decarboxylation may involves heating of the herbal composition generally below 245° F. (e.g., approximately 245° F. or lower, between 150° F. and 240° F., between 200° F. and 240° F.), so as to result in little if any vaporization of chemical compounds that may provide medicinal/therapeutic benefits, for a suitable period of time (e.g., between approximately 30-60 minutes, or longer for herbal material having a relatively higher moisture content). In some embodiments, the process of decarboxylation can be a slow, drawn out process, similar to that of curing, or else several of the more desirable compounds of the herbal composition may be lost upon vaporization.

It may be desirable for the actual time elapsed between when a container pod is placed into a receptacle and when a suitable herbal vapor is produced therefrom to be relatively short, for example. less than 10 minutes, less than 5 minutes, less than 1 minute, etc. Though, such periods of time may be shorter than the total time required for the herbal composition to undergo suitable decarboxylation. Accordingly, the packaging process of the herbal composition may, at least in part, involve decarboxylation of the herbal composition.

Hence, as described above, the manner in which *cannabis* is packaged not only allows the *cannabis* to suitably cure, but also may lend itself to decarboxylation. That is, when *cannabis* is being prepared for temporary storage within the container pod, the *cannabis* may be heated to temperatures sufficient to cause substantial decarboxylation for THC-acid to THC, but not enough to cause vaporization. In some cases, during the packaging process, even before the container pod reaches the vaporizer, a majority of the *cannabis* may already be decarboxylated. Hence, when the container pod is opened and the *cannabis* is processed within the vaporizer, the temperature within the pod may be raised to a level so as to convert the remaining THC-acid to THC.

In some embodiments, decarboxylation within the vaporizer may be characterized by a sharp increase in temperature to a temperature just below the vaporization point. For example, decarboxylation within the vaporizer may involve raising the temperature of the internal volume of the container from room temperature to within a range of between approximately 150° F. and 245° F. over a relatively short period of time (e.g., less than 5 minutes, less than 1 minute, less than 30 seconds). Though, for some embodiments, it may be preferable for this decarboxylation step by the vaporizer to occur over a longer period of time.

In some embodiments, the decarboxylation step of the vaporizer may be characterized by an increase in temperature of the herbal composition within the container pod to greater than 150° F., greater than 160° F., greater than 170° F., greater than 180° F., greater than 190° F., greater than 200° F., greater than 210° F., greater than 220° F., greater than 230° F., greater than 240° F.; or less than 250° F., less than 240° F., less than 230° F., less than 220° F., less than 210° F., less than 200° F., less than 190° F., less than 180° F., less than 160° F., or less than 150° F. Combinations of the above ranges, or values outside of these ranges, for the decarboxylation temperature may also be possible. In some cases, the decarboxylation temperature may be reached within any suitable time frame, for example, within 30 seconds, within 1 minute, within 5 minutes, within 10 minutes, etc. The decarboxylation temperature may also be held for a suitable period of time, for example, less than 60 minutes, less than 50 minutes, less than 40, less than 30 minutes, less than 20 minutes, less than 10 minutes, less than 5 minutes, less than 4 minutes, less than 3 minutes, less than 2 minutes, less than 1 minute, less than 30 seconds, etc.

Once the *cannabis* is fully or otherwise substantially decarboxylated, in preparing the system for extraction, the vaporizer may then heat the chamber to a suitable initial vaporization temperature. The appropriate initial vaporization temperature may depend, at least in part, on the particular ingredients that are present within the container pod. For example, approximate vaporization points for a number of common cannabinoids are provided in the following table:

| Cannabinoid | Vaporization Temp (° F.) |
|---|---|
| Tetrahydrocannabinol (THC) | 314.6 |
| Cannabidiol (CBD) | 320-356 |
| Cannabinol (CBN) | 365 |
| Cannabichromene (CBC) | 428 |
| Delta-8-tetrahydrocannabinol (Delta-8-THC) | 347-352.4 |
| Tetrahydrocannabivarin (THCV) | 428 |

Other compounds, such as certain flavonoids and terpenoids, may also be vaporized with the cannabinoids. Accordingly, the appropriate initial vaporization temperature may depend, at least in part, on other ingredients/compounds as well.

For example, approximate vaporization points for a number of common flavonoids are provided in the following table:

| Flavonoid | Vaporization Temp (° F.) |
|---|---|
| Beta-sitosterol | 273.2 |
| Apigenin | 352.4 |
| Cannflavin A | 359.6 |
| Quercetin | 482 |

Similarly, approximate vaporization points for a number of common terpenoids are provided in the following table:

| Terpenoid | Vaporization Temp (° F.) |
|---|---|
| Beta-caryophyllene | 390.2 |
| Alpha-terpinol | 312.8 |
| Beta-myrcene | 330.8-334.4 |
| Delta-3-carene | 334.4 |
| 1,8-cineole | 348.8 |
| D-limonene | 350.6 |
| P-cymene | 350.6 |
| Linalool | 388.4 |
| Terpinol-4-ol | 408.2 |
| Borneol | 410 |
| Alpha-terpineol | 422.6 |
| Pulegone | 435.2 |

Hence, in accordance with the vaporization/extraction recipe corresponding to the particular container pod from which herbal vapor is to be produced, the vaporizer may appropriately adjust the temperature. That is, after decarboxylation, the vaporizer may raise the temperature of the internal volume of the container pod to a temperature range just above or around that of the vaporization point of the desired compounds to be extracted. While such a temperature may be sufficient for vaporization to occur, the temperature may remain suitably below the point where denaturation and/or combustion of the herbal composition occurs.

As an example, the selected initial vaporization temperature for a high THC, low CBD/CBN container pod (e.g., approximately 320° F. or greater, between approximately 375-385° F.) may be slightly lower than that of the initial vaporization temperature selected for a low THC, high CBD/CBN container pod (e.g., approximately 370° F. or greater, between approximately 375-385° F.). Or, if the container pod includes a substantial amount of CBC or THCV, and the therapeutic/medicinal effects of these compounds is highly desirable, then the initial vaporization temperature may be comparatively higher (e.g., approximately 430° F. or greater). However, it should appreciated that the initial vaporization temperature may be appropriately optimized for each type of container pod according to a predetermined vaporization protocol, to produce an herbal vapor that elicits a preferred combination of effects.

In some embodiments, similar to that for finishing the decarboxylation step, the initial vaporization step in preparation for extraction may be characterized by another sharp increase in temperature to a temperature above the vaporization point. For example, in preparation for extraction, the vaporizer may cause an increase in temperature of the internal volume of the container pod from the decarboxylation temperature to within an appropriate range.

In some embodiments, the initial vaporization temperature in preparation for herbal extraction may be characterized by an increase in temperature of the herbal composition within the container pod to greater than 310° F., greater than 320° F., greater than 330° F., greater than 340° F., greater than 350° F., greater than 360° F., greater than 370° F., greater than 380° F., greater than 390° F., greater than 400° F., greater than 410° F., greater than 420° F., greater than 430° F., greater than 440° F., greater than 450° F., greater than 460° F., greater than 470° F., greater than 480° F.; or less than 490° F., less than 480° F., less than 470° F., less than 460° F., less than 450° F., less than 440° F., less than 430° F., less than 420° F., less than 410° F., less than 400° F., less than 390° F. (e.g., between approximately 375-385° F.), less than 380° F., less than 370° F., less than 360° F., less than 350° F., less than 340° F., less than 330° F., less than 320° F., or less than 310° F. Combinations of the above ranges, or values outside of these ranges, for the initial vaporization temperature of the herbal composition may also be possible.

In some cases, similar to that of the decarboxylation step, the initial vaporization temperature may be reached within any suitable time frame, for example, within 1 minute, within 5 minutes, within 10 minutes, etc. In some embodiments, the initial vaporization temperature may also be held for a suitable period of time, for example, at least 5 seconds, at least 10 seconds, at least 30 seconds, at least 1 minute, etc.

Once the initial vaporization temperature is reached, the temperature within the internal volume of the container pod may then be controlled by the vaporizer so as to produce an herbal vapor having a favorable combination of compounds extracted therefrom, without combustion or denaturation of the desirable herbal components. This temperature control may involve series of multiple timed temperature adjustments within the container pod.

In some embodiments, the vaporizer may cause the temperature within the internal volume to taper off at a relatively slow rate of decrease. This is in contrast to the prior stages discussed above that generally involve a sharp increase in temperature, for example, the step of decarboxylation and/or the step in temperature so as to reach the point of initial vaporization. Such gradual tapering of temperature may be suitable for extracting a favorable combination of compounds and/or flavorings from the herbal composition.

In some cases, suitable temperature conditions may result in opening and, in some cases, melting of the herbal buds so as to release the therapeutic/medicinal components and/or oils therein. Otherwise, continued heating without the temperature adjustments may lead to burning or combustion of the herbal materials. On the other hand, a sudden drop in temperature may result in limited or otherwise reduced overall extraction of a number of the more desirable herbal components.

In some embodiments, the average rate of temperature increase during herbal decarboxylation and/or during the step up to an initial vaporization temperature may be greater in magnitude than an average rate of temperature decrease during herbal extraction. For instance, the vaporizer may be configured to control the heater such that an average rate of temperature decrease during herbal extraction within the internal volume of the chamber is less than 20° F. per second, less than 15° F. per second, less than 10° F. per second, less than 9° F. per second, less than 8° F. per second, less than 7° F. per second, less than 6° F. per second, less than 5° F. per second, less than 4° F. per second, less than 3° F. per second, less than 2° F. per second, or less than 1° F. per second. It can be appreciated that other average rates of temperature decrease during the stage of herbal extraction may be possible.

The heater of the vaporizer may be controlled so as to maintain the temperature of the internal volume of the container pod within one or more ranges for a suitable period of time during the stage of herbal extraction. In some embodiments, the temperature within the internal volume of the container pod during herbal extraction may be maintained between 300° F. and 500° F., between 300° F. and 350° F., between 400° F. and 450° F., between 450° F. and 500° F., between 350° F. and 400° F., between 350° F. and 410° F., between 360° F. and 390° F., between 350° F. and 385° F., between 360° F. and 370° F., between 375° F. and 385° F. (e.g., approximately 378° F., approximately 380° F., approximately 382° F., etc.) for at least 5 seconds, at least 10 seconds, at least 15 seconds, at least 20 seconds, at least 30 seconds, at least 60 seconds, or for any other suitable period of time. It can be appreciated that other temperature ranges within the internal volume of the pod during herbal extraction may be maintained for an appropriate period of time.

In various embodiments, the temperature of the container pod may gradually decrease during herbal extraction to a final temperature which, in some cases, may be at or near room temperature. In some embodiments, while at a temperature substantially higher than the final temperature, the heater may cut out, or a cooling device may be employed, and the temperature may rapidly descend to the final temperature. Alternatively, the temperature of the container pod may slowly decrease until it reaches the final temperature.

In accordance with aspects of the present disclosure, parameters other than the temperature within the internal volume of the container pod may be controlled so as to provide conditions that result in the production of a desirable herbal vapor. For example, the relative humidity within the internal volume of the pod and the rate of air flow therethrough may be monitored and controlled.

As discussed herein, the vaporizer may be controlled to maintain the relative humidity within the internal volume of the container pod within a suitable range during each of the stages of vaporization, that is, decarboxylation, initial vaporization and herbal extraction. For example, the vaporizer may be controlled so as to maintain the relative humidity of the container pod to be similar to that during sealed storage of the herbal composition within the container pod (e.g., between approximately 50-70%, or 60-70%). Though, in some cases, the relative humidity may be adjusted according to the particular stage of vaporization. For example, the relative humidity within the container pod during decarboxylation (e.g., between approximately 60-70%) may be comparatively greater than the relative humidity during initial vaporization and herbal extraction (e.g., between approximately 40-60%). Or, the relative humidity during decarboxylation may be less than that during initial vaporization and herbal extraction.

As also provided herein, the rate of air flow through the internal volume of the container pod may be maintained within a suitable range during each of the stages of vaporization. In some embodiments, the vaporizer may be controlled so as to adjust the rate of air flow through the container pod according to the particular stage of vaporization. For example, the rate of air flow within the container pod during decarboxylation may be greater or less than the rate of air flow during initial vaporization and/or herbal extraction. In some embodiments, the rate of air flow during herbal extraction is slower than that during initial vaporization. For example, as the temperature within the container pod gradually decreases during herbal extraction, the rate of air flow may also gradually decrease. In some cases, the vaporizer generates an intermittent flow of air through the container pod during herbal extraction. Such intermittent flow, in some cases, may provide conditions that more effectively extract therapeutic/medicinal compounds from the herbal composition than would otherwise be the case without such flow.

As further shown in FIG. 16G, once the cycle(s) of herbal extraction is completed, the container pod and/or canister may be ejected from the vaporizer. For example, the user may physically remove the bag and/or canister from the vaporizer, carrying it for later consumption. Or, in some cases, the user may consume the herbal vapor directly from the vaporizer without having to remove any component. The container pod may also be suitably removed. In some cases, similar to that with respect to the canister, the user may physically remove the used container pod. Or, the vaporizer may mechanically eject the container pod from the receptacle.

It may be preferable for the container pod, and any residual contents remaining therein, to be discarded from further use. In some embodiments, the vaporizer may purposely destroy (e.g., burn, combust, discard, flush, etc.) remaining *cannabis* or other contents of the herbal composition after use. While residual materials may theoretically be reused (e.g., vaped, smoked, used for cooking), such materials may be in a degraded condition that is undesirable and/or unsafe for further usage.

Figure 16H:
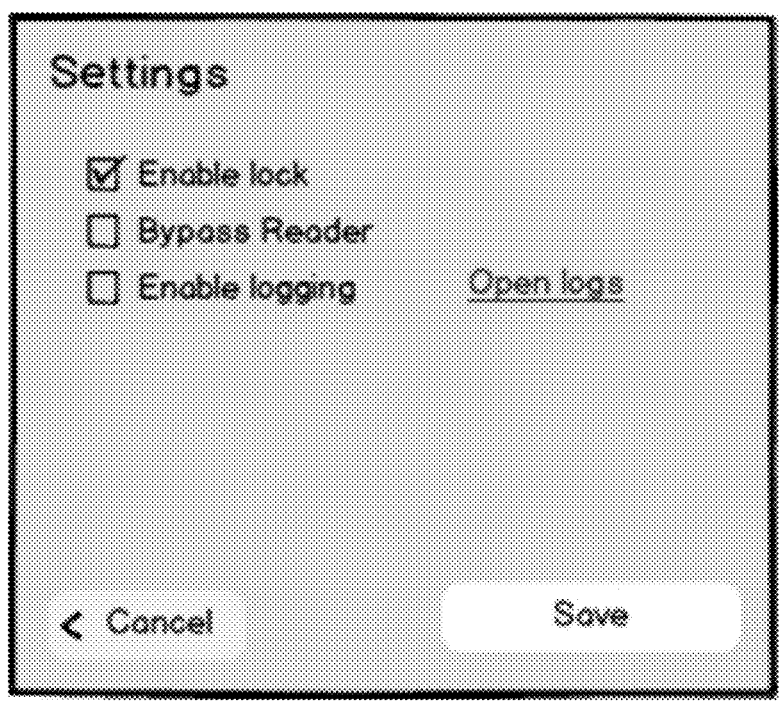

Referring back to the exemplary embodiment of the interface, FIG. 16H depicts an example of a settings screen 314, which may allow a user to adjust certain features of the vaporizer as desired. For example, a number of features which the user may have the option of whether to enable may include lock/authorization features, a digital reader which scans/collects pod information from the exterior surface of the container pod, logging features which tracks user information, etc.

Figure 16I:
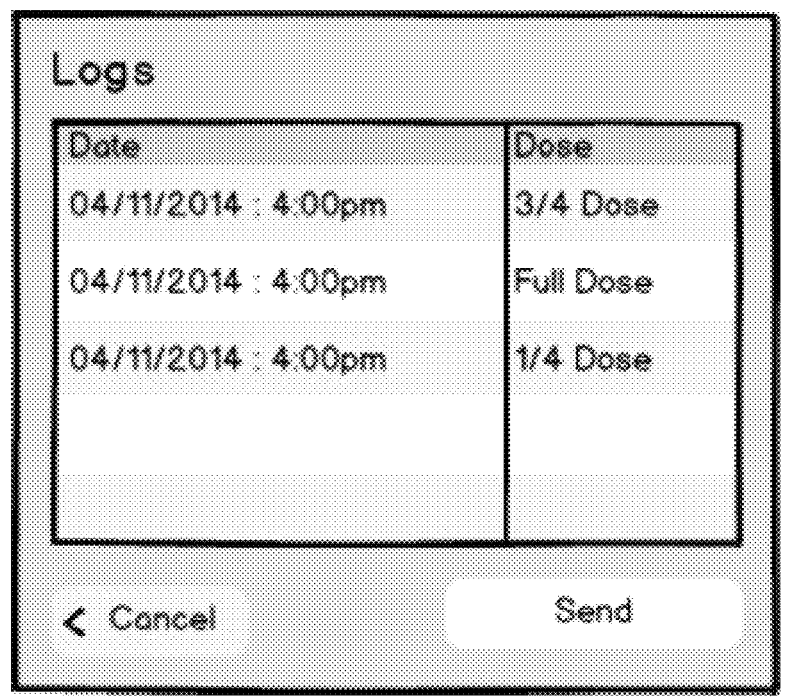

FIG. 16I shows an example of a logs screen 316 which provides a record of which dosages the patient has received. Such a record may allow the user, medical professional or other appropriate entity to track usage information, in part, to ensure that the vaporizer is being used properly and that the user is following an appropriate treatment schedule.

Figure 17:
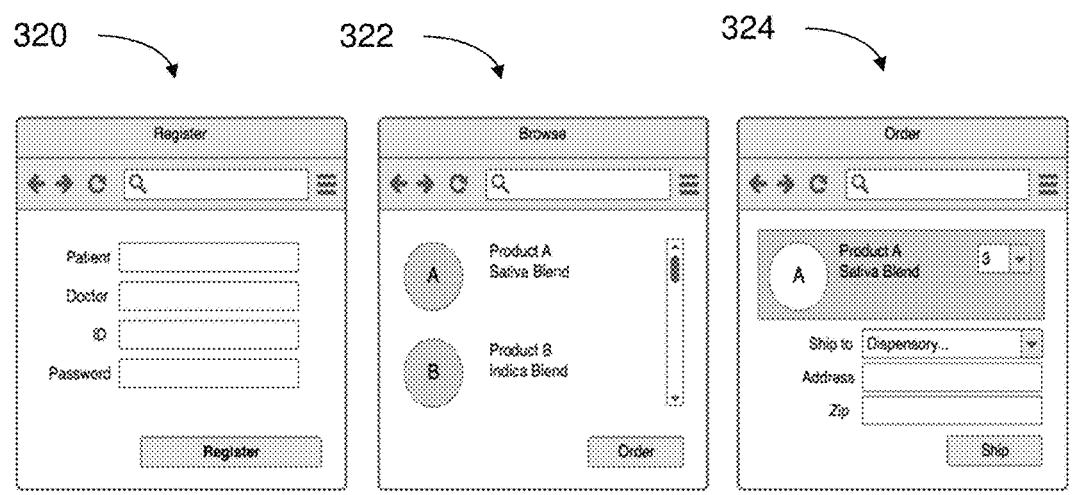
FIG. 17 show more screen shots a display interface for a vaporizer in accordance with an embodiment.

In accordance with aspects of the present disclosure, the user and/or vaporizer may be connected to a globally networked registration and distribution system for ordering, receiving and using container pods described herein. Such a system may provide the ability to track the usage of certain types of container pods, and herbal blends associated therewith, in connection with users/patients and/or medical personnel (e.g., doctors, prescribers, etc.). Thus, the system, user, medical professional, etc., may be in networked communication via a global registry and database used to process the relevant patient/medical information. In addition, systems in accordance with the present disclosure may employ analytics, statistics or other types of programming to discover and communicate meaningful patterns in the overall data collection to predict and inform patient outcomes and plans. For example, a networked database that incorporates patient health information, histories, treatment plans, or other relevant data into an integrative predictive algorithm may be helpful to understand trends, risks and likely outcomes. FIG. 17 show additional screens 320, 322, 324 that depict the ability for the vaporizer to be optionally integrated with a global registry where consumers are able to register and communicate with medical professionals and/or dispensaries. Accordingly, users may register themselves in a global database that consolidates patient and doctor information, allowing for mutual communication. Such a system may also allow consumers to browse products and order particular herbal compositions for delivery to dispensaries, stores, homes, etc. Each pod may have a unique identifier, making it possible to employ a secure, traceable registration and tracking system that controls the distribution and use of the pods.

Embodiments of the present disclosure may be used for smoking applications as well. While use of the container pod is more preferable when processed by an appropriate vaporizer machine, users may attempt to consume the contents of the herbal composition directly from the container pod itself. For example, a user may open the container pod and light the contents therein to produce smoke. To funnel the smoke into a breathable stack, rather than allowing the smoke to float away, a mouthpiece or other cigarette component may be placed over the container pod.

Figure 18:
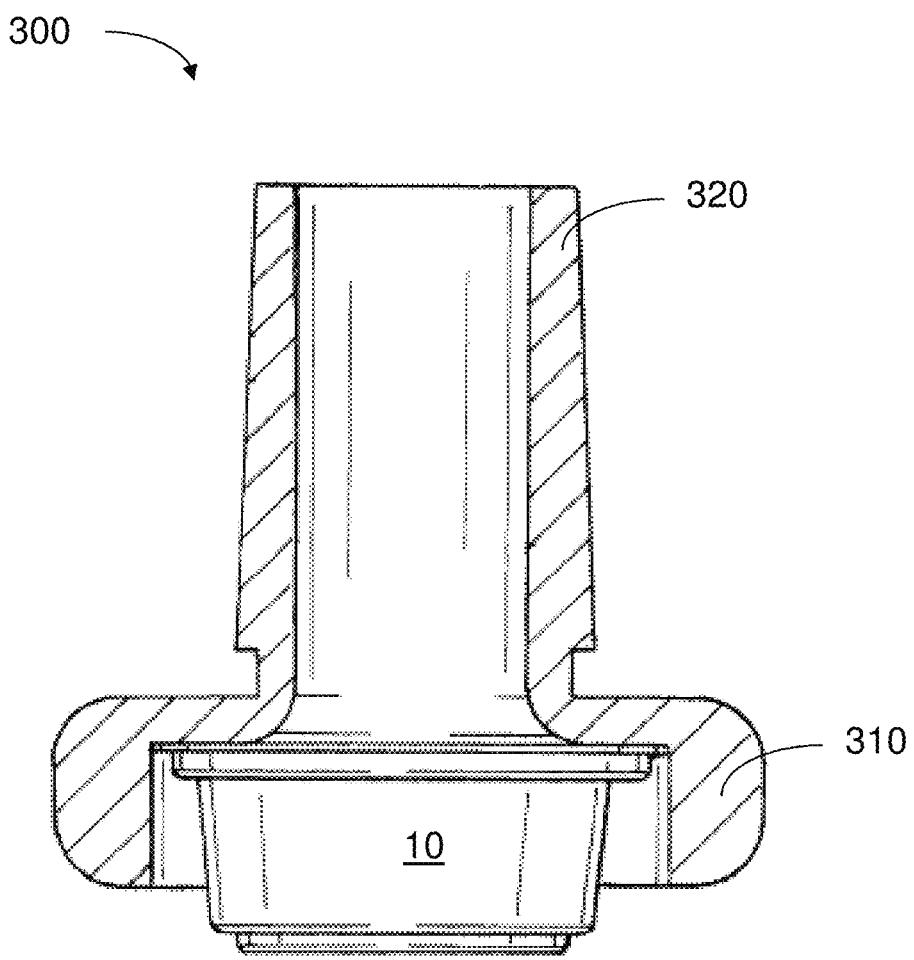
FIG. 18 depicts a cross-sectional view of a mouthpiece and a container in accordance with an embodiment.

FIG. 18 depicts an illustrative embodiment of a mouthpiece 300 adapted for coupling with a container 10 storing an herbal composition therein. The mouthpiece 300 includes a base 310 shaped to form an attachment with at least a portion of the container 10. As shown in this embodiment, the base 310 curls around the upper lid of the container 10, for suitable coupling therebetween. A pipe 320 extends from the base 310, acting as a chimney through which smoke arising from the container 10 may travel. It can be appreciated that such a mouthpiece, and suitable variations thereof, may be employed with any appropriate apparatus for consuming the herbal material. For example, the mouthpiece may be placed over a tube or opening of a water pipe, filtration device or other apparatus, for consumption thereof.

It may further be preferable for container pods described herein to be inserted within existing vaporizer machines. That is, rather than vaporizing the herbal composition within a container pod according to a pre-specified recipe that is effective to produce an herbal vapor with a combination of extracted compounds that would otherwise be unavailable, a user may decide to settle for a conventional vaporizer that requires completely manual temperature control. Though, the receptacles for conventional vaporizers may not be suitable for insertion of certain container pod embodiments. For example, rather than being configured to receive a container pod having pre-specified herbal contents, the receptacle of a conventional vaporizer may be designed for herbal leaves to be inserted directly therein. In some cases, such a design may have an awkward shape that is not ideal for fitting of a container pod therein. Accordingly, an adapter may be employed to retrofit a conventional vaporizer to receive container pods in accordance with the present disclosure.

Figure 19:
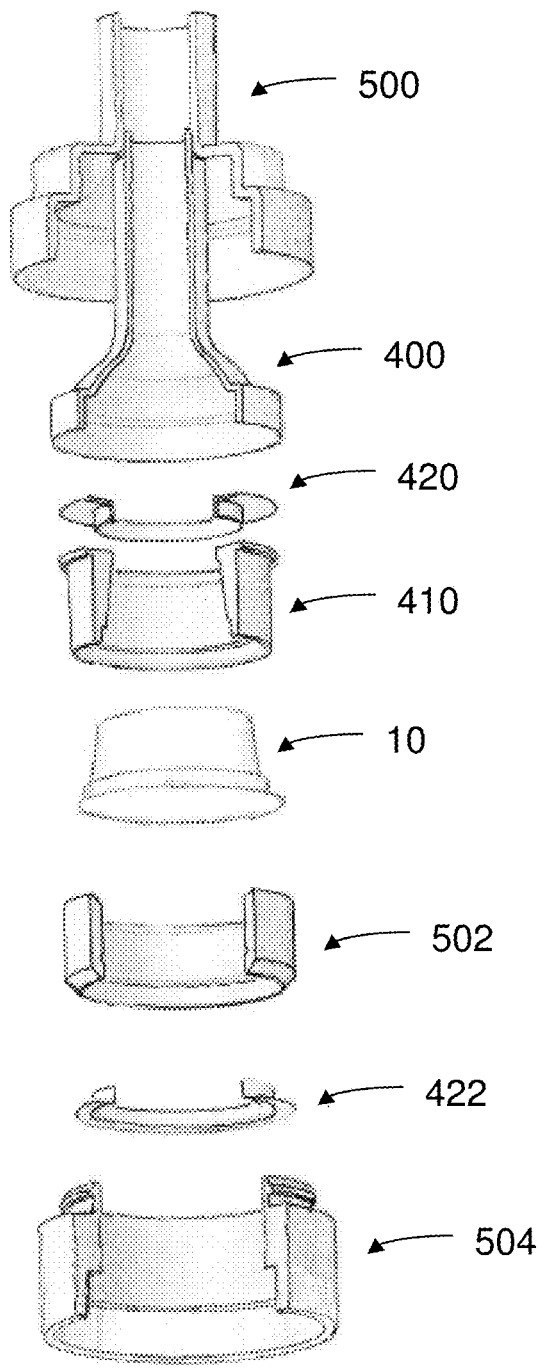
FIG. 19 depicts an exploded perspective cut-away view of an adapter for a container holding an herbal composition in accordance with an embodiment.
Figure 20:
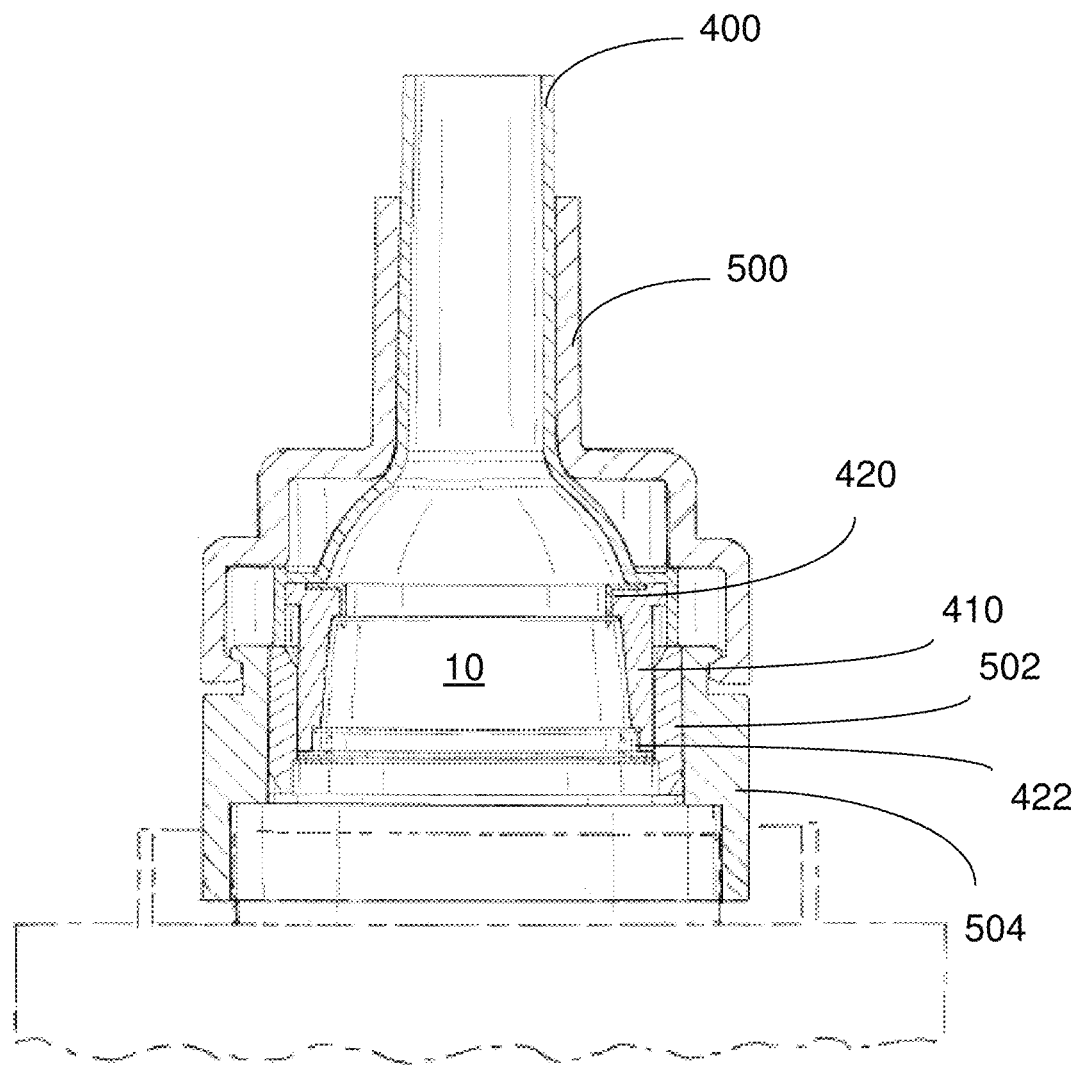
FIG. 20 illustrates a cross-sectional view of an adapter for a container holding an herbal composition in accordance with an embodiment.

FIGS. 19 and 20 depict an illustrative embodiment of an adapter that may be placed within the receptacle of a conventional vaporizer, to accept a container pod where the container pod would not otherwise fit in a suitable manner. As shown, the adapter components 400, 410, 420, 422 may be placed within a space provided by various parts 500, 502, 504 of a conventional vaporizer, for subsequent insertion of a container 10. The conventional vaporizer includes a funnel 500, a chamber wall 502 and a base 504, forming a receptacle that is intended to receive raw herbal material directly therein, without any such container.

The adapter includes a complementary funnel 400 that may be screwed, attached or otherwise coupled to the funnel 500 of the conventional vaporizer. The adapter also includes a sleeve 410, which fits into the space provided by the chamber wall 502, and is constructed to house the container 10. The adapter further includes sharp edge components 420, 422, configured to be positioned on opposite sides of the sleeve 410. The sharp edge components 420, 422 include edges that protrude into the space of the sleeve 410 within which the container 10 is placed. Upon positioning of the container 10 into this space, the sharp edge components 420, 422 configured to pierce the respective lids of the container 10, exposing the contents held therein for vaporization. It can be appreciated that any suitable adapter configuration may be employed.

Having thus described several aspects of at least one embodiment of this invention, it is to be appreciated various alterations, modifications, and improvements will readily occur to those skilled in the art. For example, the devices described herein may be adapted for use in medical or non-medically related applications. Such alterations, modification, and improvements are intended to be part of this disclosure, and are intended to be within the spirit and scope of the invention. Accordingly, the foregoing description and drawings are by way of example only.

What is claimed is:

1. A container for producing an herbal vapor, comprising:
 a chamber having a wall defining an internal volume and a boundary that seals the internal volume from an external environment, the chamber being arranged to be removably received in a receptacle of a vaporizer and the wall being arranged to receive heat from a heater of the receptacle that is transferred through the wall and into the internal volume for vaporization;
 an herbal composition located within the internal volume of the chamber and exposed for contact with at least a portion of an inner side of the wall;
 at least one filter located within the internal volume of the chamber constructed and arranged to filter vapor produced from the herbal composition or trap particles of the herbal composition; and
 a support member located within the internal volume of the chamber, for holding and distributing the herbal composition within the internal volume to avoid collection or accumulation of the herbal composition at a bottom of the container during vaporization, the support member including a metal and arranged to provide heat to the herbal composition in the internal volume.

2. The container of claim 1, wherein the support member includes at least one of stainless steel wool, a coiled structure, a metallic ribbon, a mesh screen, ball bearings and a divider.

3. The container of claim 1, wherein the support member is adapted to produce heat by electromagnetic induction.

4. The container of claim 1, wherein the herbal composition includes *cannabis*.

5. The container of claim 4, wherein the *cannabis* includes a tetrahydrocannabinol content of less than 25 wt % and a combined cannabidiol and cannabinol content of less than 25 wt %.

6. The container of claim 1, wherein the herbal composition includes at least one of terpenes, flavonoids, mint, chamomile, ginko and mango.

7. The container of claim 1, further comprising readable information located on an exterior surface of the container including information regarding contents of the herbal composition located within the internal volume of the chamber.

8. The container of claim 1, wherein the at least one filter includes a first filter located at an upper end of the internal volume and a second filter located at a lower end of the internal volume.

9. The container of claim 1, wherein the at least one filter includes a wire screen mesh filter.

10. The container of claim 1, wherein the at least one filter has an average pore size of between 1 mil and 50 mil.

11. The container of claim 1, wherein the at least one filter has an average pore size at least 10% smaller than an average particle size of the herbal composition.

12. The container of claim 1, further comprising a dividing wall that partitions the internal volume of the chamber into multiple sub-chambers.

13. The container of claim 1, further comprising a lid forming the seal between the internal volume of the chamber and the external environment.

14. The container of claim 1, wherein the support member suspends the herbal composition above the bottom of the container.

15. The container of claim 1, wherein the bottom of the container is piercable to permit air flow into the internal volume.

16. The container of claim 1, further comprising a lid having a peel tab and that is removable from an upper opening of the chamber.

17. The container of claim 1, further comprising a lid defining the bottom of the container.

* * * * *